United States Patent
Vanmechelen et al.

(10) Patent No.: US 7,387,879 B2
(45) Date of Patent: Jun. 17, 2008

(54) DIAGNOSIS OF TAUOPATHIES

(75) Inventors: Eugeen Vanmechelen, Nazareth-Eke (BE); Hugo Vanderstichele, Ghent (BE)

(73) Assignee: Innogenetics N.V., Ghent (BE)

( * ) Notice: Subject to any disclaimer, the term of this patent is extended or adjusted under 35 U.S.C. 154(b) by 715 days.

(21) Appl. No.: 10/682,103

(22) Filed: Oct. 9, 2003

(65) Prior Publication Data

US 2004/0091942 A1    May 13, 2004

Related U.S. Application Data

(62) Division of application No. 09/769,180, filed on Jan. 24, 2001, now Pat. No. 6,680,173.

(60) Provisional application No. 60/178,391, filed on Jan. 27, 2000.

(30) Foreign Application Priority Data

Jan. 24, 2000  (EP)  .................................. 00870008
Nov. 22, 2000  (EP)  ................................ 000870280

(51) Int. Cl.
    *G01N 33/53*    (2006.01)
    *G07K 7/06*     (2006.01)
    *G07K 14/435*   (2006.01)

(52) U.S. Cl. ...................... 435/7.1; 435/975; 530/324; 530/329; 530/330

(58) Field of Classification Search ................. 435/7.1, 435/975; 530/324, 329, 330
See application file for complete search history.

(56) References Cited

FOREIGN PATENT DOCUMENTS

| WO | WO 93/03369 | 2/1993 |
|----|-------------|--------|
| WO | WO 94/13795 | 6/1994 |
| WO | WO 94/18560 | 8/1994 |
| WO | WO 95/17429 | 6/1995 |
| WO | WO 96/04309 | 2/1996 |
| WO | WO 97/34145 | 9/1997 |
| WO | WO 99/62548 | 12/1999 |

OTHER PUBLICATIONS

Rudinger, In *Peptide Hormones*. J.A. Parsons, ed. University Park Press, Baltimore, 1976.*

* cited by examiner

*Primary Examiner*—Jeffrey Stucker
*Assistant Examiner*—Stephen Gucker
(74) *Attorney, Agent, or Firm*—Howrey LLP

(57) ABSTRACT

The present invention provides a method for the diagnosis of tauopathies in an individual and/or for the differential diagnosis of a tauopathy versus a non-tauopathy based on the detection of the ratio of phospho-tau (181)/total tau in said individual. The present invention further provides a phospho-peptide for standardization in a method of the invention.

13 Claims, 10 Drawing Sheets

SEQUENCE LISTING

<160> NUMBER OF SEQ ID NOS: 54

<210> SEQ ID NO 1
<211> LENGTH: 5
<212> TYPE: PRT
<213> ORGANISM: Homo sapiens

<400> SEQUENCE: 1

Pro Pro Gly Gln Lys
1               5

<210> SEQ ID NO 2
<211> LENGTH: 7
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 2

Pro Pro Ala Pro Lys Thr Pro
1               5

<210> SEQ ID NO 3
<211> LENGTH: 34
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: PHOSPHORYLATION

<400> SEQUENCE: 3

Pro Arg Gly Ala Ala Pro Pro Gly Gln Lys Gly Gln Ala Asn Ala Thr
1               5                   10                  15

Arg Ile Pro Ala Lys Thr Pro Pro Ala Pro Lys Thr Pro Pro Ser Ser
            20                  25                  30

Gly Glu

<210> SEQ ID NO 4
<211> LENGTH: 35
<212> TYPE: DNA
<213> ORGANISM: Homo sapiens

<400> SEQUENCE: 4
catggctgag ccccgccagg agttcgaagt gatgg                              35

<210> SEQ ID NO 5
<211> LENGTH: 32
<212> TYPE: DNA
<213> ORGANISM: Homo sapiens

<400> SEQUENCE: 5
cctgatcaca aaccctgctt ggccagggag gc                                 32

<210> SEQ ID NO 6
<211> LENGTH: 6
<212> TYPE: PRT
<213> ORGANISM: Homo sapiens

<400> SEQUENCE: 6

Asp Arg Ser Gly Tyr Ser

```
1               5

<210> SEQ ID NO 7
<211> LENGTH: 7
<212> TYPE: PRT
<213> ORGANISM: Homo sapiens

<400> SEQUENCE: 7

Pro Pro Thr Arg Glu Pro Lys
1               5

<210> SEQ ID NO 8
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 8

Lys Gly Ala Asp Gly Lys Thr Lys Ile Ala Thr Pro Arg Gly Ala Ala
1               5                   10                  15

Pro Pro Gly Gln Lys
            20

<210> SEQ ID NO 9
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 9

Gln Ala Asn Ala Thr Arg Ile Ala Pro Lys Thr Pro Pro Ala Pro Lys
1               5                   10                  15

Thr Pro Pro Ser Ser
            20

<210> SEQ ID NO 10
<211> LENGTH: 22
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION

<400> SEQUENCE: 10

Arg Ile Pro Ala Lys Thr Pro Pro Ala Pro Lys Thr Pro Pro Ser Ser
1               5                   10                  15

Gly Glu Pro Pro Lys Ser
            20

<210> SEQ ID NO 11
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 11
```

-continued

Pro Pro Lys Ser Gly Asp Arg Ser Gly Tyr Ser Ser Gly Ser Pro Gly
1               5                   10                  15

Thr Pro Gly Ser Arg
            20

<210> SEQ ID NO 12
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 12

Pro Lys Ser Gly Asp Arg Ser Gly Tyr Ser Ser Gly Ser Pro Gly Thr
1               5                   10                  15

Pro Gly Ser Arg Ser
            20

<210> SEQ ID NO 13
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 13

Ser Gly Asp Arg Ser Gly Tyr Ser Ser Gly Ser Pro Gly Thr Pro Gly
1               5                   10                  15

Ser Arg Ser Arg Thr
            20

<210> SEQ ID NO 14
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 14

Arg Ser Gly Tyr Ser Ser Gly Ser Pro Gly Thr Pro Gly Ser Arg Ser
1               5                   10                  15

Arg Thr Pro Ser Leu
            20

<210> SEQ ID NO 15
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 15

Tyr Ser Ser Gly Ser Pro Gly Thr Pro Gly Ser Arg Ser Arg Thr Pro
1               5                   10                  15

Ser Leu Pro Thr Pro
            20

```
<210> SEQ ID NO 16
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 16

Ser Gly Ser Pro Gly Thr Pro Gly Ser Arg Ser Arg Thr Pro Ser Leu
1               5                   10                  15

Pro Thr Pro Thr Arg
            20

<210> SEQ ID NO 17
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 17

Ser Pro Gly Thr Pro Gly Ser Arg Ser Arg Thr Pro Ser Leu Pro Thr
1               5                   10                  15

Pro Thr Arg Glu Pro
            20

<210> SEQ ID NO 18
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 18

Gly Thr Pro Gly Ser Arg Ser Arg Thr Pro Ser Leu Pro Thr Pro Thr
1               5                   10                  15

Arg Glu Pro Lys Lys
            20

<210> SEQ ID NO 19
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 19

Gly Ser Arg Ser Arg Thr Pro Ser Leu Pro Thr Pro Thr Arg Glu Pro
1               5                   10                  15

Lys Lys Val Ala Val
            20

<210> SEQ ID NO 20
<211> LENGTH: 20
<212> TYPE: PRT
<213> ORGANISM: Homo sapiens
<220> FEATURE:
<221> NAME/KEY: MOD_RES
<222> LOCATION: (11)..(11)
```

```
<223> OTHER INFORMATION: PHOSPHORYLATION

<400> SEQUENCE: 20

Arg Glu Pro Lys Lys Val Ala Val Val Arg Thr Pro Lys Ser Pro Ser
1               5                   10                  15

Ser Ala Lys Ser
            20

<210> SEQ ID NO 21
<211> LENGTH: 20
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 21

Lys Lys Val Ala Val Val Arg Thr Pro Lys Ser Pro Ser Ser Ala Lys
1               5                   10                  15

Ser Arg Leu Gln
            20

<210> SEQ ID NO 22
<211> LENGTH: 12
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 22

Val Lys Ser Lys Ile Gly Ser Thr Glu Asn Leu Lys
1               5                   10

<210> SEQ ID NO 23
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 23

Thr Asp His Gly Ala Glu Ile Val Tyr Lys Ser Pro Val Val Ser Asp
1               5                   10                  15

Thr Ser Pro Arg His
            20

<210> SEQ ID NO 24
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 24

Ala Glu Ile Val Tyr Lys Ser Pro Val Val Ser Asp Thr Ser Pro Arg
1               5                   10                  15

His Leu Ser Asn Val
            20
```

```
<210> SEQ ID NO 25
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 25

Ile Val Tyr Lys Ser Pro Val Val Ser Asp Thr Ser Pro Arg His Leu
1               5                   10                  15

Ser Asn Val Ser Ser
            20

<210> SEQ ID NO 26
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION

<400> SEQUENCE: 26

Tyr Lys Ser Pro Val Val Ser Asp Thr Ser Pro Arg His Leu Ser Asn
1               5                   10                  15

Val Ser Ser Thr
            20

<210> SEQ ID NO 27
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 27

Val Val Ser Asp Thr Ser Pro Arg His Leu Ser Asn Val Ser Ser Thr
1               5                   10                  15

Gly Ser Ile Asp Met
            20

<210> SEQ ID NO 28
<211> LENGTH: 21
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 28

Asp Thr Ser Pro Arg His Leu Ser Asn Val Ser Ser Thr Gly Ser Ile
1               5                   10                  15

Asp Met Val Asp Ser
            20

<210> SEQ ID NO 29
<211> LENGTH: 21
<212> TYPE: PRT
<213> ORGANISM: Homo sapiens
<220> FEATURE:
<221> NAME/KEY: MOD_RES
```

```
<222> LOCATION: (11)..(11)
<223> OTHER INFORMATION: PHOSPHORYLATION

<400> SEQUENCE: 29

Ser Ser Thr Gly Ser Ile Asp Met Val Asp Ser Pro Gln Leu Ala Thr
1               5                   10                  15

Leu Ala Asp Glu Val
            20

<210> SEQ ID NO 30
<211> LENGTH: 78
<212> TYPE: PRT
<213> ORGANISM: Homo sapiens

<400> SEQUENCE: 30

Arg Gly Ala Ala Pro Pro Gly Gln Lys Gly Gln Ala Asn Ala Thr Arg
1               5                   10                  15

Ile Pro Ala Lys Thr Pro Pro Ala Pro Lys Thr Pro Pro Ser Ser Gly
            20                  25                  30

Glu Pro Pro Lys Ser Gly Asp Arg Ser Gly Tyr Ser Ser Pro Gly Ser
        35                  40                  45

Pro Gly Thr Pro Gly Ser Arg Ser Arg Thr Pro Ser Leu Pro Thr Pro
    50                  55                  60

Pro Thr Arg Glu Pro Lys Lys Val Ala Val Val Arg Thr Pro
65                  70                  75

<210> SEQ ID NO 31
<211> LENGTH: 9
<212> TYPE: PRT
<213> ORGANISM: Homo sapiens

<400> SEQUENCE: 31

Arg Gly Ala Ala Pro Pro Gly Gln Lys
1               5

<210> SEQ ID NO 32
<211> LENGTH: 9
<212> TYPE: PRT
<213> ORGANISM: Homo sapiens

<400> SEQUENCE: 32

Gly Ala Ala Pro Pro Gly Gln Lys Gly
1               5

<210> SEQ ID NO 33
<211> LENGTH: 9
<212> TYPE: PRT
<213> ORGANISM: Homo sapiens

<400> SEQUENCE: 33

Ala Ala Pro Pro Gly Gln Lys Gly Gln
1               5

<210> SEQ ID NO 34
<211> LENGTH: 9
<212> TYPE: PRT
<213> ORGANISM: Homo sapiens

<400> SEQUENCE: 34

Ala Pro Pro Gly Gln Lys Gly Gln Ala
1               5
```

```
<210> SEQ ID NO 35
<211> LENGTH: 9
<212> TYPE: PRT
<213> ORGANISM: Homo sapiens

<400> SEQUENCE: 35

Pro Pro Gly Gln Lys Gly Gln Ala Asn
1               5

<210> SEQ ID NO 36
<211> LENGTH: 9
<212> TYPE: PRT
<213> ORGANISM: Homo sapiens

<400> SEQUENCE: 36

Lys Ser Gly Asp Arg Ser Gly Tyr Ser
1               5

<210> SEQ ID NO 37
<211> LENGTH: 9
<212> TYPE: PRT
<213> ORGANISM: Homo sapiens

<400> SEQUENCE: 37

Ser Gly Asp Arg Ser Gly Tyr Ser Ser
1               5

<210> SEQ ID NO 38
<211> LENGTH: 9
<212> TYPE: PRT
<213> ORGANISM: Homo sapiens

<400> SEQUENCE: 38

Gly Asp Arg Ser Gly Tyr Ser Ser Pro
1               5

<210> SEQ ID NO 39
<211> LENGTH: 9
<212> TYPE: PRT
<213> ORGANISM: Homo sapiens

<400> SEQUENCE: 39

Asp Arg Ser Gly Tyr Ser Ser Pro Gly
1               5

<210> SEQ ID NO 40
<211> LENGTH: 12
<212> TYPE: PRT
<213> ORGANISM: Homo sapiens

<400> SEQUENCE: 40

Pro Ser Leu Pro Thr Pro Pro Thr Arg Glu Pro Lys
1               5                   10

<210> SEQ ID NO 41
<211> LENGTH: 12
<212> TYPE: PRT
<213> ORGANISM: Homo sapiens

<400> SEQUENCE: 41

Ser Leu Pro Thr Pro Pro Thr Arg Glu Pro Lys Lys
1               5                   10

<210> SEQ ID NO 42
<211> LENGTH: 12
```

-continued

```
<212> TYPE: PRT
<213> ORGANISM: Homo sapiens

<400> SEQUENCE: 42

Leu Pro Thr Pro Pro Thr Arg Glu Pro Lys Lys Val
1               5                   10

<210> SEQ ID NO 43
<211> LENGTH: 12
<212> TYPE: PRT
<213> ORGANISM: Homo sapiens

<400> SEQUENCE: 43

Pro Thr Pro Pro Thr Arg Glu Pro Lys Lys Val Ala
1               5                   10

<210> SEQ ID NO 44
<211> LENGTH: 12
<212> TYPE: PRT
<213> ORGANISM: Homo sapiens

<400> SEQUENCE: 44

Thr Pro Pro Thr Arg Glu Pro Lys Lys Val Ala Val
1               5                   10

<210> SEQ ID NO 45
<211> LENGTH: 12
<212> TYPE: PRT
<213> ORGANISM: Homo sapiens

<400> SEQUENCE: 45

Pro Pro Thr Arg Glu Pro Lys Lys Val Ala Val Val
1               5                   10

<210> SEQ ID NO 46
<211> LENGTH: 15
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION

<400> SEQUENCE: 46

Ala Thr Arg Ile Pro Ala Lys Thr Pro Pro Ala Pro Lys Thr Pro
1               5                   10                  15

<210> SEQ ID NO 47
<211> LENGTH: 15
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: PHOSPHORYLATION

<400> SEQUENCE: 47

Thr Arg Ile Pro Ala Lys Thr Pro Pro Ala Pro Lys Thr Pro Pro
1               5                   10                  15

<210> SEQ ID NO 48
<211> LENGTH: 15
<212> TYPE: PRT
<213> ORGANISM: Homo sapiens
<220> FEATURE:
<221> NAME/KEY: MOD_RES
<222> LOCATION: (12)..(12)
```

```
<223> OTHER INFORMATION: PHOSPHORYLATION

<400> SEQUENCE: 48

Arg Ile Pro Ala Lys Thr Pro Pro Ala Pro Lys Thr Pro Pro Ser
1               5                   10                  15

<210> SEQ ID NO 49
<211> LENGTH: 15
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: PHOSPHORYLATION

<400> SEQUENCE: 49

Ile Pro Ala Lys Thr Pro Pro Ala Pro Lys Thr Pro Pro Ser Ser
1               5                   10                  15

<210> SEQ ID NO 50
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION

<400> SEQUENCE: 50

Pro Ala Lys Thr Pro Pro Ala Pro Lys Thr Pro Pro Ser Ser Gly
1               5                   10                  15

<210> SEQ ID NO 51
<211> LENGTH: 15
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 51

Ala Lys Thr Pro Pro Ala Pro Lys Thr Pro Pro Ser Ser Gly Glu
1               5                   10                  15

<210> SEQ ID NO 52
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 52

Lys Thr Pro Pro Ala Pro Lys Thr Pro Pro Ser Ser Gly Glu Pro
1               5                   10                  15

<210> SEQ ID NO 53
<211> LENGTH: 15
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 53
```

```
Thr Pro Pro Ala Pro Lys Thr Pro Pro Ser Ser Gly Glu Pro Pro
1               5                   10                  15

<210> SEQ ID NO 54
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 54

Pro Pro Ala Pro Lys Thr Pro Pro Ser Ser Gly Glu Pro Pro Lys
1               5                   10                  15
```

DIAGNOSIS OF TAUOPATHIES

This is a divisional of application Ser. No. 09/769,180, filed 24 Jan. 2001, now U.S. Pat. No. 6,680,173 which claims priority to EP 00870008.0, filed 24 Jan. 2000; U.S. provisional application Ser. No. 60/178,391, filed 27 Jan. 2000; and EP 00870280.5, filed 22 Nov. 2000.

FIELD OF THE INVENTION

The present invention relates to the diagnosis of tauopathies. The present invention provides a new method for the detection and/or differential diagnosis of tauopathies. The present invention also provides a phospho-peptide that can be used for standardization in a method of the invention.

BACKGROUND OF THE INVENTION

Several forms of dementia, the so-called tauopathies (Goedert et al., 1998), have been associated with the same pathophysiological mechanism, the involvement of the structural protein tau. The microtubule-associated protein tau is for example a major protein component of paired helical filaments (PHF) and neurofibrillar tangles (NFT), associated with Alzheimer's disease (Brion et al., 1985; Delacourte and Defossez, 1986;

Grundke-Iqbal et al., 1986; Kosik et al., 1986; Wood et al., 1986; Kondo et al., 1988). Tau protein exists in different isoforms, of which 4 to 6 are found in adult brain but only 1 isoform is detected in fetal brain. The diversity of the isoforms is generated from a single gene on human chromosome 17 by alternative mRNA splicing (Himmler, 1989; Goedert et al., 1989; Andreadis et al., 1992). The most striking feature of tau protein, as deduced from molecular cloning, is a stretch of 31 or 32 amino acids, occurring in the carboxy-terminal part of the molecule, which can be repeated either 3 or 4 times. Additional diversity is generated through 29 or 58 amino acid-long insertions in the $NH_2$-terminal part of tau molecules (Goedert et al., 1989). In vivo tau promotes microtubule assembly and stability in the axonal compartment of neurons by interactions involving its microtubule binding domain which is localized in the repeat region of tau (255-381) (Lewis et al., 1988). In normal circumstances adult brain contains 2-3 mole phosphate per mole of tau (Selden and Pollard, 1983; Ksiezak-Reding et al., 1992). Phosphorylation of different sites in normal tau as studied in rat and humans is dependent on the developmental state (Lee et al., 1991; Bramblett et al., 1993; Goedert et al., 1993). Tau variants of 60, 64 and 68 kDa arising as a consequence of phosphorylation have been detected in brain areas showing neurofibrillary tangles (Delacourte et al., 1990; Goedert et al., 1992; Flament et al., 1990, Greenberg and Davies, 1990). These brains contain 6-8 mole phosphate per mole tau (Ksiezak-Reding et al., 1992). In tau isolated from PHF (PHF-tau), phosphorylation occurs at several positions (Iqbal et al., 1989; Lee et al., 1991; Hasegawa et al., 1992; Hanger et al., 1998; Buee et al., 1999).

Alzheimer's disease (AD) is the most common type of primary degenerative dementia associated with a tau pathology, having a prevalence of 42-75% (Brun, 1993; Gustafson, 1993; Ebly et al., 1994). Frontotemporal dementia (FTD) is a clinical condition in which pathologically Pick's disease, Frontotemporal dementia with Parkinsonism linked to chromosome 17, sporadic FTD and motor neuron disease are present. According to a small study by Mann et al. (2000), 16 of the 37 cases with FTD could be classified as tauopathy based on tau-immunohistochemistry. Filamentous tau pathology i.e. neurofibrillary tangles (NFT), are consistently found in AD (Tomlinson and Corsellis, 1984) but may also be found in FTD (Spillantini and Goedert, 1998). Pathological tau proteins are found both in AD and FTD (Vermersch et al., 1995; Delacourte et al., 1996), however studies on brain tissue have suggested that the tau pathology differs between AD and FTD, possibly being related to the degree of phosphorylation (Delacourte et al., 1996). Other forms of dementia associated with a tau pathology include Progressive supranuclear palsy (PSP), Corticobasal degeneration (CBD) and Subacute sclerosing panencephalitis. The role of hyperphosphorylation in the pathology of these tauopathies is at present not well understood. In addition, various difficulties have been encountered in the accurate determination of the degree of phosphorylation of specific phospho-sites concentrated in the proline region. Because of these difficulties, an accurate method for the specific detection of these tauopathies is still lacking.

SUMMARY OF THE INVENTION

The present invention relates to a method for the diagnosis of a tauopathy in an individual, said method involving:
  determining the ratio of phospho-tau (181)/total tau in said individual;
  inferring that said individual is suffering a tauopathy by comparing the obtained ratio of phospho-tau (181)/total tau in said individual with the ratio of phospho-tau (181)/total tau in control individuals, whereby an altered ratio of phospho-tau (181)/total tau compared to said ratio in control individuals being an indication of tauopathy.

The present invention also relates to a method for the differential diagnosis of a tauopathy versus a non-tauopathy in an individual, said method involving:
  determining the ratio of phospho-tau (181)/total tau in said individual; inferring that said individual is suffering a tauopathy by comparing the obtained ratio of phospho-tau (181)/total tau in said individual with the ratio of phospho-tau (181)/total tau in individuals suffering a non-tauopathy or with the phospho-tau (181)/total tau ratio in control individuals, whereby an altered ratio of phospho-tau (181)/total tau compared to said ratio in individuals suffering a non-tauopathy or in control individuals being an indication of tauopathy.

It is an aim of the present invention to provide a method for the diagnosis of a tauopathy in an individual.

It is another aim of the present invention to provide a method for the diagnosis of Alzheimer's disease, Pick's disease, sporadic Frontotemporal dementia and/or Frontotemporal dementia with Parkinsonism linked to chromosome 17 in an individual.

It is another aim of the present invention to provide a method for the differential diagnosis of a tauopathy versus a non-tauopathy.

It is another aim of the present invention to provide a method for the differential diagnosis of a tauopathy versus a non-tauopathy neurodegeneration.

It is another aim of the present invention to provide a method for the differential diagnosis of a tauopathy versus vascular dementia, Creutzfeldt Jacob Disease, stroke and/or neurotoxicity in patients with leukemia.

It is another aim of the present invention to provide a method for the differential diagnosis of Alzheimer's disease, Pick's disease, sporadic Frontotemporal dementia and/or Frontotemporal dementia with Parkinsonism linked to chromosome 17 versus vascular dementia, Creutzfeldt Jacob Disease, stroke and/or neurotoxicity in patients with leukemia.

It is another aim of the present invention to provide an in vitro method as described above.

It is another aim of the present invention to provide a phospho-peptide for use in standardization.

It is another aim of the present invention to provide a phospho-peptide for use in standardization in a method to detect phospho-tau (181).

It is another aim of the present invention to provide a phospho-peptide for use in standardization in a method as described above.

It is another aim of the present invention to provide a diagnostic kit for use in a method as described above.

It is another aim of the present invention to provide a peptide, a method and/or a diagnostic kit for the testing or screening of drugs, for therapeutic monitoring and/or for the determination of the effectiveness of a certain treatment for a tauopathy.

TABLE 1

Figure 1:
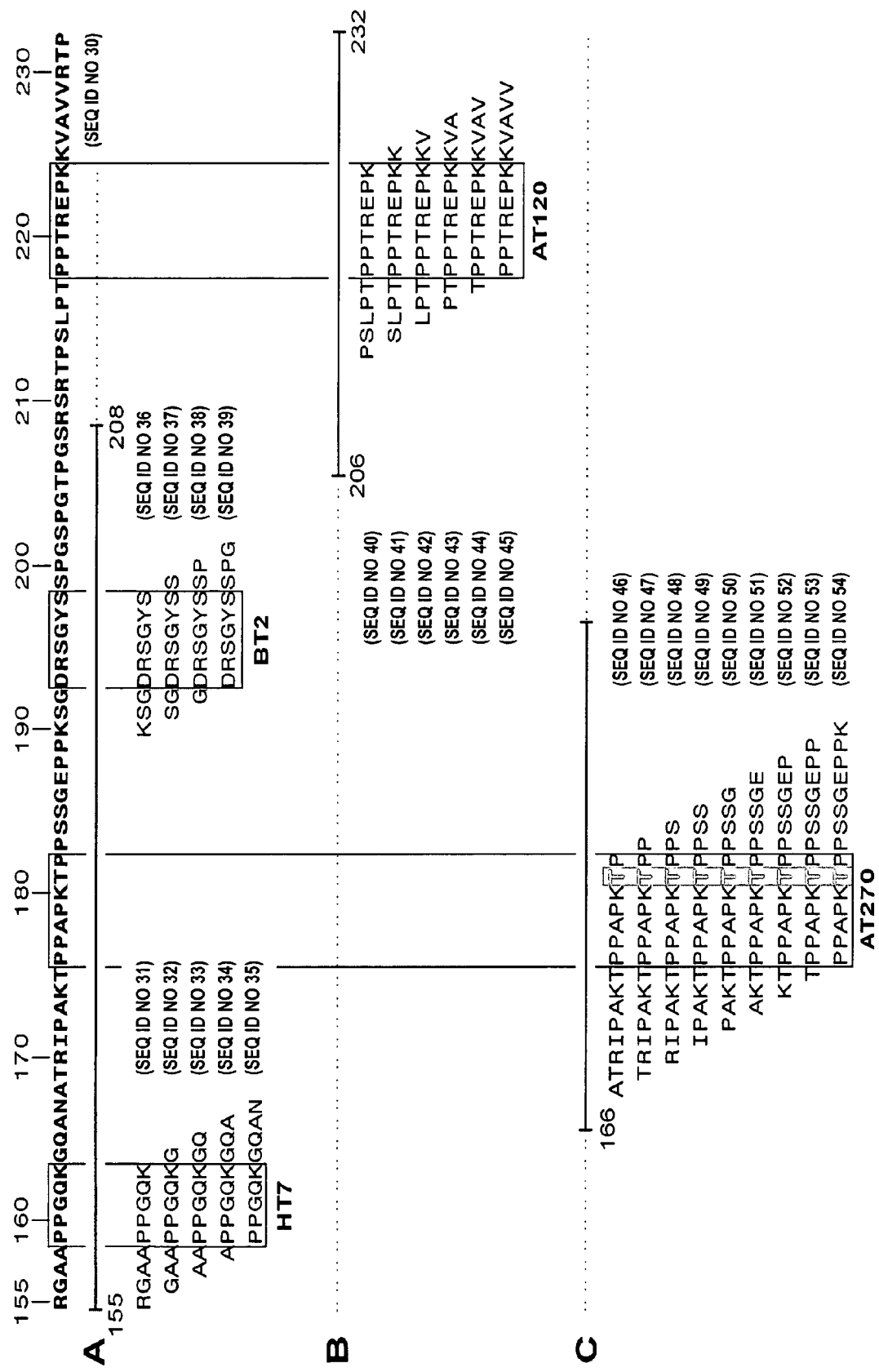
FIG. 1. Fine mapping of tau antibodies, HT7, tau1, BT2, AT120 and AT270 on overlapping synthetic peptides. Only immunoreactive peptides are shown. A. Mapping on peptides synthesized on pins. 48 nonapeptides overlapping 8 amino acids were used to cover the tau region from 155 till 208. B. Peptide synthesis on paper. Sixteen overlapping peptides, 12 amino acids long define the AT120 epitope in the region 206-232. C. Mapping of the AT270 antibody on biotinylated phosphopeptides (the phosphorylated threonine is indicated) covering the region 166 until 196.

Sequence of the phosphorylated peptides used to determine the specificity of AT270 for phospho-Thr 181.

| Name | Sequence | SEQ ID NO |
|---|---|---|
| 153 | LysGlyAlaAspGlyLysThrLysIleAlaThr(p)ProArgGlyAlaAlaProProGlyGlnLys | 8 |
| 175 | GlnAlaAsnAlaThrArgIleAlaProLysThr(p)ProProAlaProLysThrProProSerSer | 9 |
| 181 | ArgIleProAlaLysThrProProAlaProLysThr(p)ProProSerSerGlyGlyProLysSer | 10 |
| 198 | ProProLysSerGlyAspArgSerGlyTyrSer(p)SerGlySerProGlyThrProGlySerArg | 11 |
| 199 | ProLysSerGlyAspArgSerGlyTyrSerSer(p)GlySerProGlyThrProGlySerArgSer | 12 |
| 202 | SerGlyAspArgSerGlyTyrSerSerGlySer(p)ProGlyThrProGlySerArgSerArgThr | 13 |
| 205 | ArgSerGlyTyrSerSerGlySerProGlyThr(p)ProGlySerArgSerArgThrProSerLeu | 14 |
| 208 | TyrSerSerGlySerProGlyThrProGlySer(p)ArgSerArgThrProSerLeuProThrPro | 15 |
| 210 | SerGlySerProGlyThrProGlySerArgSer(p)ArgThrProSerLeuProThrProThrArg | 16 |
| 212 | SerProGlyThrProGlySerArgSerArgThr(p)ProSerLeuProThrProThrArgGluPro | 17 |
| 214 | GlyThrProGlySerArgSerArgThrProSer(p)LeuProThrProThrArgGluProLysLys | 18 |
| 217 | GlySerArgSerArgThrProSerLeuProThr(p)ProThrArgGluProLysLysValAlaVal | 19 |
| 231 | ArgGluProLysLysValAlaValValArgThr(p)ProLysSerProSerSerAlaLysSer | 20 |
| 235 | LysLysValAlaValValArgThrProLysSer(p)ProSerSerAlaLysSerArgLeuGln | 21 |
| 262 | ValLysSerLysIleGlySer(p)ThrGluAsnLeuLys | 22 |
| 396 | ThrAspHisGlyAlaGluIleValTyrLysSer(p)ProValValSerAspThrSerProArgHis | 23 |
| 400 | AlaGluIleValTyrLysSerProValValSer(p)AspThrSerProArgHisLeuSerAsnVal | 24 |
| 403 | IleValTyrLysSerProValValSerAspThr(p)SerProArgHisLeuSerAsnValSerSer | 25 |
| 404 | TyrLysSerProValValSerAspThrSer(p)ProArgHisLeuSerAsnValSerSerThr | 26 |
| 409 | ValValSerAspThrSerProArgHisLeuSer(p)AsnValSerSerThrGlySerIleAspMet | 27 |
| 412 | AspThrSerProArgHisLeuSerAsnValSer(p)SerThrGlySerIleAspMetValAspSer | 28 |
| 422 | SerSerThrGlySerIleAspMetValAspSer(p)ProGlnLeuAlaThrLeuAlaAspGluVal | 29 |

(p): amino acid is phosphorylated.

TABLE 2

Clinical characteristics of patients involved in the study described in example 2.

| Diagnosis | N | Gender (M:F) | Age | Duration dementia (y) | Degree of dementia[a] | Albumin ratio[b] |
|---|---|---|---|---|---|---|
| FTD | 18 | 5:13 | 65.5 ± 8.4 | 4.1 ± 3.2 | 17.7 ± 6.4 | 9.7 ± 2.9 |
| Prob AD | 41 | 13:28 | 73.8 ± 5.9 | 3.2 ± 1.8 | 17.6 ± 5.2 | 5.4 ± 1.8 |
| Poss AD | 19 | 11:8 | 78.9 ± 5.7 | 3.0 ± 2.3 | 21.9 ± 3.7 | 7.9 ± 2.9 |
| SAE | 17 | 12:5 | 75.8 ± 4.4 | 2.6 ± 2.2 | 22.1 ± 7.2 | 11.9 ± 7.2 |
| PD | 15 | 11:4 | 69.9 ± 7.5 | — | — | 6.8 ± 2.4 |
| Controls | 17 | 4:13 | 71.8 ± 4.2 | — | — | 5.3 ± 1.8 |

[a]MMSE-score;
[b]Albumin ration = [CSF-albumin (mg/L)/serum-albumin (g/L)].
All values are expressed as means ± SD. The following abbreviations are used:
FTD: Frontotemporal dementia;
AD: Alzheimer's disease;
SAE: Subcortical artheriosclerotic encephalopathy;
PD: Parkinson's disease;
Prob: probable;
Poss: possible;
N: number of individuals;
M: male;
F: female;
y: years;
CSF: cerebrospinal fluid.

TABLE 3

CSF-levels of total tau, phospho-tau (181) and phospho-tau (181)/total tau ratio in dementia disorders, Parkinson's disease and normal aging.

| | Cerebrospinal fluid levels (pM) | | |
|---|---|---|---|
| Diagnosis | Total tau | Phospho-tau (181) | Phospho tau (181)/total tau |
| FTD | 9.74 ± 2.88 | 8.59 ± 3.88*** | 0.88 ± 0.34*** |
| Probable AD | 20.01 ± 7.58*** | 23.12 ± 10.10** | 1.16 ± 0.24*** |
| Possible AD | 16.34 ± 4.30*** | 18.01 ± 5.86 | 1.10 ± 0.20*** |
| SAE | 3.70 ± 2.29*** | 6.39 ± 5.59*** | 1.96 ± 1.08 |
| PD | 7.45 ± 1.59 | 14.07 ± 3.11 | 1.92 ± 0.42 |
| Controls | 8.33 ± 2.83 | 15.92 ± 5.72 | 1.95 ± 0.60 |

All values are expressed as means ± SD.
Abbreviations: FTD: Frontotemporal dementia; AD: Alzheimer's disease; PD: Parkinson's disease; SAE: Subcortical artheriosclerotic encephalopathy.
***Value is significantly different compared to the value for controls ($p < 0.001$).
**Value is significantly different compared to the value for controls ($p < 0.01$).
*Value is significantly different compared to the value for controls ($p < 0.05$).

DETAILED DESCRIPTION OF THE INVENTION

The present invention relates to a method for the diagnosis of a tauopathy in an individual, said method comprising the step of:
  determining the ratio of phospho-tau (181)/total tau in said individual;
  inference that said individual is suffering a tauopathy by comparing the obtained ratio of phospho-tau (181)/total tau in said individual with the ratio of phospho-tau (181)/total tau in control individuals, an altered ratio of phospho-tau (181)/total tau compared to said ratio in control individuals being an indication.

The present invention also relates to a method for the differential diagnosis of a tauopathy versus a non-tauopathy in an individual, said method comprising the steps of:
  determining the ratio of phospho-tau (181)/total tau in said individual;
  inference that said individual is suffering a tauopathy by comparing the obtained ratio of phospho-tau (181)/total tau in said individual with the ratio of phospho-tau (181)/total tau in individuals suffering a non-tauopathy or with the phospho-tau (181)/total tau ratio in control individuals, an altered ratio of phospho-tau (181)/total tau compared to said ratio in individuals suffering a non-tauopathy or in control individuals being an indication.

The present invention is based on the finding that the ratio of phospho-tau (181)/total tau in CSF from patients suffering AD and in CSF from patients suffering certain forms of FTD is significantly altered compared to the phospho-tau (181)/total tau ratio in CSF from control individuals. The present invention is further based on the finding that the ratio of phospho-tau (181)/total tau in CSF from patients suffering AD is significantly altered compared to the phospho-tau (181)/total tau ratio in CSF from patients suffering stroke. The indication that the phospho-tau (181)/total tau ratio in patients with a tauopathy is altered, forms a basis for the development of a diagnostic test for the diagnosis of a tauopathy in an individual and/or for the differential diagnosis of individuals suffering a tauopathy versus individuals suffering a non-tauopathy.

'A tauopathy' is any form of dementia that is associated with a tau pathology.

Alzheimer's disease and certain forms of Frontotemporal dementia (Pick's disease, sporadic Frontotemporal dementia and Frontotemporal dementia with Parkinsonism linked to chromosome 17) are the most common forms of tauopathy. In accordance, the present invention relates to any method as described above, wherein the tauopathy is Alzheimer's, Pick's disease, sporadic Frontotemporal dementia and Frontotemporal dementia with Parkinsonism linked to chromosome 17. Other tauopathies include but are not limited to Progressive supranuclear palsy (PSP), Corticobasal degeneration (CBD) and Subacute sclerosing panencephalitis.

In a specific embodiment, the present invention relates to a method for the diagnosis of Azheimer's disease in an individual, said method comprising the steps of:
  determining the ratio of phospho-tau (181)/total tau in said individual;
  inference that said individual is suffering Alzheimer's disease by comparing the obtained ratio of phospho-tau (181)/total tau in said individual with the ratio of phospho-tau (181)/total tau in control individuals, an altered ratio of phospho-tau (181)/total tau compared to said ratio in control individuals being an indication.

A 'non-tauopathy' is any status of the brain that is not associated with a tau pathology. In an embodiment of the invention, said non-tauopathy is a non-tauopathy neurodegeneration. A non-tauopathy neurodegeneration is any form of neurological disorder that is not associated with a tau pathology. Non-tauopathy neurodegenerations include but are not limited to vascular dementia, Creutzfeldt Jacob Disease, stroke and/or neurotoxicity in patients with leukemia.

Therefore, in a specific embodiment, the present invention relates to a method for the differential diagnosis in an individual of Alzheimer's disease versus stoke, said method comprising the steps of:
  determining the ratio of phospho-tau (181)/total tau in said individual;

inference that said individual is suffering Alzheimer's disease and not stroke by comparing the obtained ratio of phospho-tau (181)/total tau in said individual with the ratio of phospho-tau (181)/total tau in individuals suffering a stroke, an altered ratio of phospho-tau (181)/total tau compared to said ratio in individuals suffering a stroke being an indication.

Phospho-tau (181) includes all tau molecules that carry a phosphate on the threonine at position 181. The numbering with respect to the amino acid sequence refers to the longest tau isoform hTau40 (Goedert et al., 1989).

Total tau refers to all forms of tau and includes tau in any state of phosphorylation.

The present invention thus relates to tau and phospho-tau (181) for use as neurological markers for the diagnosis of a tauopathy and/or for the differential diagnosis of a tauopathy versus a non-tauopathy.

Based on the level of phospho-tau (181) and total tau in an individual, the ratio of phospho-tau (181)/total tau in said individual can then be determined.

The ratio of phospho-tau (181)/total tau can be detected in vitro as well as in vivo.

The method for the in vitro detection of the ratio of phospho-tau (181)/total tau in an individual comprises the steps of:
   obtaining a sample from said individual;
   determining the ratio of phospho-tau (181)/total tau in said sample;
   inference that said individual is suffering a tauopathy by comparing the obtained ratio of phospho-tau (181)/total tau in said individual with the phospho-tau (181)/total tau ratio in a sample from individuals suffering a non-tauopathy or with the phospho-tau (181)/total tau ration in a sample from control individuals, an altered ratio of phospho-tau (181)/total tau compared to said ratio in individuals suffering a non-tauopathy or in control individuals being an indication.

The term 'sample' refers to any source of biological material, for instance body fluids, brain extract, peripheral blood or any other sample comprising phospho-tau (181) protein. In an embodiment of the invention, the ratio of phospho-tau (181)/total tau is determined in vitro by analysis of the ratio of phospho-tau (181)/total tau in a body fluid sample of the patient. The term 'body fluid' refers to all fluids that are present in the human body including but not limited to blood, lymph, urine and cerebrospinal fluid (CSF) comprising phospo-tau (181) protein. In another embodiment of the present invention the ratio of phospho-tau (181)/total tau is determined in a cerebrospinal fluid (CSF) sample taken from the patient. In accordance, the present invention relates to a method as described above, comprising the steps of:
   obtaining a cerebrospinal fluid sample from the individual;
   determining the ratio of phospho-tau (181)/total tau in said cerebrospinal fluid sample;
   inference that said individual is suffering a tauopathy by comparing the obtained ratio of phospho-tau (181)/total tau in said individual with the ratio of phospho-tau (181)/total tau in the CSF from individuals suffering a non-tauopathy or with the phospho-tau (181)/total tau ratio in the CSF from control individuals, an altered ratio of phospho-tau (181)/total tau compared to said ratio in the CSF from individuals suffering a non-tauopathy or in the CSF from control individuals being an indication.

Total tau can be quantified by any method known, including but not limited to the use of antibodies or else by a functional assay (Bramblett et al., 1992). Any monoclonal or polyclonal antibody that specifically recognizes total tau may be used for the quantification of total tau. Antibodies recognizing normally and abnormally phosphorylated tau include Alz50 (Ghanbari et al., 1990), HT7 (Mercken et al., 1992) and AT120 (Vandermeeren et al., 1993). But also other antibodies known in the art which recognize total tau can be used. A very fast and user-friendly method for the quantification of total tau is the INNOTEST hTau-Ag (Innogenetics, Gent, Belgium). Phospho-tau (181) can be quantified by any method known in the art, including but not limited to the use of antibodies. In a preferred embodiment, phospho-tau (181) is quantified by an immunoassay comprising at least the following steps:
   obtaining a sample from the patient;
   bringing said sample into contact with a monoclonal antibody specifically recognizing phospho-tau (181), under conditions being suitable for producing an antigen-antibody complex;
   detecting the immunological binding of said antibody to said sample.

In an even more preferred embodiment, phospho-tau (181) can be quantified by a sandwich ELISA comprising the following steps:
   obtaining a sample from the patient;
   bringing said sample into contact with a monoclonal antibody (primary antibody or capturing antibody) recognizing phospho-tau (181), under conditions being suitable for producing an antigen-antibody complex;
   bringing said sample into contact with a monoclonal antibody (secondary antibody or detector antibody) specifically recognizing phospho-tau (181), under conditions being suitable for producing an antigen-antibody complex;
   bringing the antigen-antibody complex into contact with a marker either for specific tagging or coupling with said secondary antibody, with said marker being any possible marker known to the person skilled in the art;
   possibly also, for standardization purposes, bringing the antibodies in contact with a purified phospho-tau protein or phospho-peptide reactive with both antibodies.

Advantageously, the secondary antibody itself carries a marker or a group for direct or indirect coupling with a marker.

The expression 'recognizing', 'reacting with', 'immunological binding' or 'producing an antigen-antibody complex' as used in the present invention is to be interpreted that binding between the antigen and antibody occurs under all conditions that respect the immunological properties of the antibody and the antigen.

The expression 'specifically recognizing' as used in the present invention is to be interpreted that said antibody is capable of forming an immunological complex with phospho-tau (181) but not with a tau molecule that lacks the phosphorylation at threonine 181.

Any monoclonal antibody that specifically recognizes phospho-tau (181) can be used in said method for the quantification of phospho-tau (181). A preferred monoclonal antibody for use in the quantification of phospho-tau (181) is AT270 (International application published under WO 95/17429). But also other antibodies known in the art that specifically recognize phospho-tau (181) can be used.

For standardization purposes, a tau protein or peptide phosphorylated at threonine 181 can be used. This can be obtained by any method such as extraction from brain or in vitro phosphorylation of normal tau. Since it is difficult to determine accurately the degree of phosphorylation of specific phospho-sites concentrated in the proline region, in an embodiment of the invention, a synthetic phospho-peptide is used for standardization. Said synthetic phospho-peptide should be able to form an immunological complex with the antibodies used in the immunoassay.

The present invention thus also relates to a phospho-peptide comprising at least two epitopes that are recognized by a monoclonal antibody, said phospho-peptide being liable to form an immunological complex with said monoclonal antibodies in a sandwich ELISA. Previous work has shown that, although a peptide contains an epitope for a certain monoclonal antibody, said monoclonal antibody does not always recognize said peptide (DeLeys et al., 1996). The present inventors were able to define a phospho-peptide with two epitopes such, that indeed said phospho-peptide is able to form an immunological complex with the monoclonal antibodies recognizing said epitopes. In addition, the present inventors were able to define both epitopes such that the phospho-peptide is able to form an immunological complex with the monoclonal antibodies recognizing said epitopes in a sandwich ELISA.

The term 'peptide' refers to a polymer of amino acids (aa) and does not refer to a specific length of the product. In an embodiment of the invention, the length for the phospho-peptide is between 15 and 100 amino acid. In a preferred embodiment of the invention, the phospho-peptide contains 20 to 50 amino acids. In another preferred embodiment of the invention, the phospho-peptide contains 30 to 40 amino acids.

The peptide of the invention can be produced by any method known in the art such as classical chemical synthesis as described by Houbenweyl (1974) and Atherton and Shepard (1989), by any commercially available method such as described in the examples section, or by means of recombinant DNA techniques as described by Sambrook et al. (1989).

A phospho-peptide is a peptide that carries a phosphate on at least one amino acid. The use of the phospho-peptide of the invention allowed the present inventors to determine the relation of phospho-peptide to specific phospho isoforms and to assess the degree of phosphorylation of specific phospho-sites (see example 1, 1.5). The use of the phospho-peptide of the invention will allow the quantification of particular molecular forms of tau in a standardized way.

Phosphorylated peptides can be made by any method known. They can be made post-assembly, by reaction for example with di-t-butyl diisopropyl diisopropylphosphoara-midite and oxidation with t-butyl hydroperoxide of unprotected serine and threonine residues. They can also be made by incorporation of phosphorylated amino acids during peptide synthesis. Recently, new phosphorylated serine derivatives (N-α-Fmoc-O-benzyl-L-phosphoSer) are commercially available (Calbiochem-Novabiochem AG, San Diego, Calif. 92121) to synthesize directly phosphopeptides without post-assembly phosphorylation.

In an embodiment, the present invention relates to a phospho-peptide liable to form an immunological complex with monoclonal antibody HT7 and monoclonal antibody AT270, comprising at least:
the minimal epitope of HT 7: ProProGlyGlnLys (SEQ ID NO 1); and
the minimal epitope of AT270: ProProAlaProLysThr(p)Pro (SEQ ID NO 2).

In an even more preferred embodiment, the present invention relates to a phospho-peptide as described above, comprising the following sequence:

```
ProArgGlyAlaAlaProProGlyGlnLysGlyGlnAlaAsnAlaThr

ArgIleProAlaLysThrProProAlaProLysThr(p)ProProSer

SerGlyGlu (SEQ ID NO 3)
``` wherein '(p)' signifies that threonine is phosphorylated, or variant sequences on the condition that they still bind to the HT7 and AT270 monoclonal antibodies. The term 'variant sequences' refers to any variant or fragment of the peptide represented in SEQ ID NO 3, by substitution or deletion of one or more amino acids, which still recognizes the HT7 and AT270 monoclonal antibodies. The term does not specifically refer to, nor does it exclude, post-translational modifications of the peptide such as glycosylation, acetylation, phosphorylation, modifications with fatty acid and the like. Included in the definition are, for example, peptides containing one or more analogues of an amino acid (including unnatural amino acids), peptides with substituted linkages, mutated versions, peptides containing disulfide bounds between cysteine residues, biotinylated peptides as well as other modifications known in the art.

The present invention further relates to the use of said phospho-peptide in a method for measuring the level of phospho-tau (181).

The present invention further relates to the use of said phospho-peptide in a method for the diagnosis of a tauopathy and/or for the differential diagnosis of a tauopathy versus a non-tauopathy.

The present invention further relates to the use of said phospho-peptide in a method for the diagnosis of Alzheimer's disease.

The present invention further relates to the use of said phospho-peptide in a method for the differential diagnosis of Alzheimer's disease versus stroke.

The method for the in vitro detection of the ratio of phospho-tau (181)/total tau in an individual can also be used for testing or screening of drugs, for therapeutic monitoring and/or to evaluate the effect of a certain treatment on the tauopathy in said individual.

The method for the early in vivo detection of the ratio of phospho-tau (181)/total tau in an individual comprises the steps of determining the ratio of phospho-tau (181)/total tau in said individual and comparing it to the ratio of phospho-tau (181)/total tau in control healthy individuals. In an embodiment, phospho-tau (181) and total tau can be quantified by in vivo imaging. Phospho-tau (181) and total tau can be quantified in situ by non-invasive methods including but not limited to brain imaging methods described by Arbit et al. (1995), Tamada et al. (1995), Wakabayashi et al. (1995), Huang et al. (1996), Sandrock et al. (1996), Mariani et al. (1997). These in vivo imaging methods may allow the localization and quantification of phospho-tau (181) and total tau, for example, by use of labeled antibodies respectively specifically recognizing phospho-tau (181) or recognizing total tau.

Phospho-tau (181) and total tau can also be used as markers for in vivo imaging for testing or screening of drugs, for therapeutic monitoring and/or to evaluate the effect of a certain treatment on the tauopathy in said individual.

The present invention further relates to a diagnostic kit for the diagnosis of a tauopathy in an individual and/or for the differential diagnosis of a tauopathy versus a non-tauopathy comprising at least an antibody specifically recognizing phospho-tau (181).

In another embodiment, the present invention relates to a diagnostic kit as described above comprising at least:
an antibody specifically recognizing phospho-tau (181);
an antibody recognizing tau.

In another embodiment, the present invention relates to a diagnostic kit as described above comprising at least a phospho-peptide according to the invention.

In another embodiment, the present invention relates to a diagnostic kit as described above comprising at least:
- an antibody specifically recognizing phospho-tau (181);
- a phospho-peptide according to the invention.

In another embodiment, the present invention relates to a diagnostic kit as described above comprising at least:
- an antibody specifically recognizing phospho-tau (181);
- an antibody recognizing tau;
- a phospho-peptide according to the invention.

A preferred kit for the diagnosis of a tauopathy in an individual is based on an immunoassay and comprises:
- a monoclonal antibody (primary antibody) which forms an immunological complex with an epitope of phospho-tau (181);
- a monoclonal antibody (secondary antibody) which specifically recognizes phospho-tau (181);
- a marker either for specific tagging or coupling with said secondary antibody;
- appropriate buffer solutions for carrying out the immunological reaction between the primary antibody and the test sample, between the secondary antibody and the test sample and/or between the bound secondary antibody and the marker;
- a phospho-peptide according to the invention.

The present invention further relates to the use of a diagnostic kit as described above for the diagnosis of a tauopathy in an individual and/or for the differential diagnosis of a tauopathy versus a non-tauopathy.

The present invention further relates to the use of a diagnostic kit as described above for the diagnosis of Alzheimer's disease, Pick's disease, sporadic Frontotemporal dementia and/or Frontotemporal dementia with Parkinsonism linked to chromosome 17.

The present invention further relates to the use of a diagnostic kit as described above for the differential diagnosis of Alzheimer's disease, Pick's disease, sporadic Frontotemporal dementia and/or Frontotemporal dementia with Parkinsonism linked to chromosome 17 versus vascular dementia, Creutzfeldt Jacob Disease, stroke and/or neurotoxicity in patients with leukemia.

The present invention also relates to the use of total tau and phospho-tau (181) as neurological markers for the manufacture of a diagnostic kit for the diagnosis of a tauopathy and/or for the differential diagnosis of a tauopathy versus a non-tauopathy.

The present invention also relates to the use of a phospho-peptide, a method and/or a diagnostic kit of the invention for the testing or screening of drugs, for therapeutic monitoring and/or for the determination of the effectiveness of a certain treatment for a tauopathy.

Throughout this specification and the claims which follow, unless the context requires otherwise, the word "comprise", and variations such as "comprises" and "comprising", will be understood to imply the inclusion of a stated integer or step or group of stated integers or steps but not to the exclusion of any other integer or step or group of integers or steps.

The reference to any prior art in this specification is not, and should not be taken as an acknowledgment or any form of suggestion that that prior art forms part of the common general knowledge in Australia.

The present invention will now be illustrated by reference to the following examples that set forth particularly advantageous embodiments. However, it should be noted that these examples are illustrative and can not be construed as to restrict the invention in any way.

EXAMPLES

Example 1

Design of a Phospho-peptide for use in Standardization 1.1 Synthesis of Tau and Tau-derived Peptides Two PCR primers (a primer containing the starting methionine codon—CATGGCTGAGCCCCGCCAG-GAGTTCGAAGTGATGG (−1 to 34) (SEQ ID NO 4) and the reverse primer around the stop codon CCTGATCA-CAAACCCTGCTTGGCCAGGGAGGC (SEQ ID NO 5)) were used to amplify the smallest form from human tau into a $P_L$-based expression system (Innogenetics, Gent, Belgium). The sequence of the PCR product was confirmed by sequencing. Changes were only observed at the third basepair in codons: at Pro 182 CAG instead of CAA, at Ala 227 GCG instead of GCA, and at Asn 251 AAC instead of AAT. All numbering with respect to the amino acid sequence refers to the longest tau isoform: hTau40 (Goedert et al., 1989). Deletion mutants were made based on constructing frameshift mutants by filling in the SacII site (amino acid position 154-155) and the PstI site (position 242-243).

Automated peptide synthesis was performed on a Millipore 9050 synthesizer, usually as N-terminally biotinylated peptides. Large-scale synthesis of peptide AcProArgGlyAlaAlaProProGlyGlnLysGlyGlnAlaAsnAlaThrArgIleProAlaLysThrProProA laProLysThr(p)ProProSerSerGlyGlu-NH$_2$ (position 154-187) (SEQ ID NO 3) for sandwich ELISA was synthesized in house and by Neosystems (Strasbourg, France). Quality control includes RP-HPLC (reverse-phase high-pressure liquid chromatography) (>99% pure), mass-spectrometer analysis (average MW 3454.8), and amino acid analysis (Net peptide content 84.3%).

For epitope mapping, peptides were synthesized manually on derivatized pins (Multiple Peptide Systems, San Diego, Calif. 92121) or on paper. For peptides synthesized on paper, the paper was derivatized using the symmetric anhydride of Fmoc-β-alanine (9-fluorenylmethoxycarbonyl-β-alanine) in the presence of dimethyl aminopyridine. After removal of the Fmoc group, a second β-alanine residue was added following activation with TBTU (=2-(1H-benzotriazole-1-yl)-1,1',3,3'-tetramethyluronium tetrafluoroborate). Peptides were subsequently synthesized manually as spots.

Phosphorylated peptides were made by post-assembly reaction with di-t-butyl diisopropyl diisopropylphosphoaramidite and oxidation with t-butyl hydroperoxide of unprotected serine and threonine residues. Recently, new phosphorylated serine derivatives (N-α-Fmoc-O-benzyl-L-phosphoSer) are commercially available (Calbiochem-Novabiochem AG, San Diego, Calif. 92121) to synthesize directly phosphopeptides without post-assembly phosphorylation. After detachment from the solid support, peptides and phosphopeptides were purified by reverse-phase high-performance liquid chromatography (RP-HPLC). The quality of the peptides was verified by mass spectrometry.

1.2 Immunoassays

Details of the isolation and characterization of antibodies have been described for AT120 (Vandermeeren et al., 1993b), HT7 (Mercken et al., 1992), BT2 (Vandermeeren et al., 1993a) and AT270 (Goedert et al., 1994). To quantify peptide-antibody interactions by capturing assay, streptavidin (Roche Diagnostics, Brussels, Belgium) was coated at 5 µg/ml overnight in 50 mM carbonate buffer, pH 9.5. After blocking, biotinylated peptides were added and detected with the tau antibodies. A second antibody coupled to horseradish peroxidase was used to quantify the immunoreaction.

The research version of the INNOTEST phospho-tau (181P) was designed as follows: HT7-coated immunoplates were incubated overnight at 4° C. with 75 μl sample or standard, simultaneously with biotinylated AT270. After washing, horseradish peroxidase-labeled streptavidin (RDI, Flanders, N.J., US) is added for 30 min. The reaction is stopped by addition of 50 μl 0.9 N $H_2SO_4$.

Total tau was measured using the INNOTEST hTau-Ag, and a calculated molecular weight of 41065 for recombinant tau, which was used as standard was employed to convert pg/ml to pM.

1.3 Mapping of Tau Antibodies

In order to map the tau antibodies recognizing recombinant tau on the complete tau molecule, deletion mutants were constructed based on the PstI and SacII sites. The antibodies tested, i.e. HT7, AT120, BT2 and tau1, all map to the proline-rich region (position 154-242 on hTau40, results not shown). To further delineate the epitopes, small overlapping peptides were synthesized. In a first step, 48 peptides, 9 amino acids long and overlapping 8 amino acids were synthesized on pins. The sequence ranged from 155 until 208. AT120, HT7, BT2 and tau1 were tested. Four of the five antibodies could be mapped: the minimal epitope of HT7 was ProProGlyGlnLys (position 159-163) (SEQ ID NO 1), while the reactivities of BT2 and tau-1 were indistinguishable: AspArgSerGlyTyrSer (position 193-198) (SEQ ID NO 6) (FIG. 1a). Since AT120 could not be mapped on these peptides, a new set of peptides was synthesized on paper, covering the sequence from 206-232. A total of 16 peptides, 12 amino acids-long, and overlapping with 11 amino acids, were needed to cover this region. The minimal epitope of AT120 was defined by the sequence ProProThrArgGluProLys (position 218-224) (SEQ ID NO 7) (FIG. 1b).

1.4 Specificity of AT270

Figure 2:
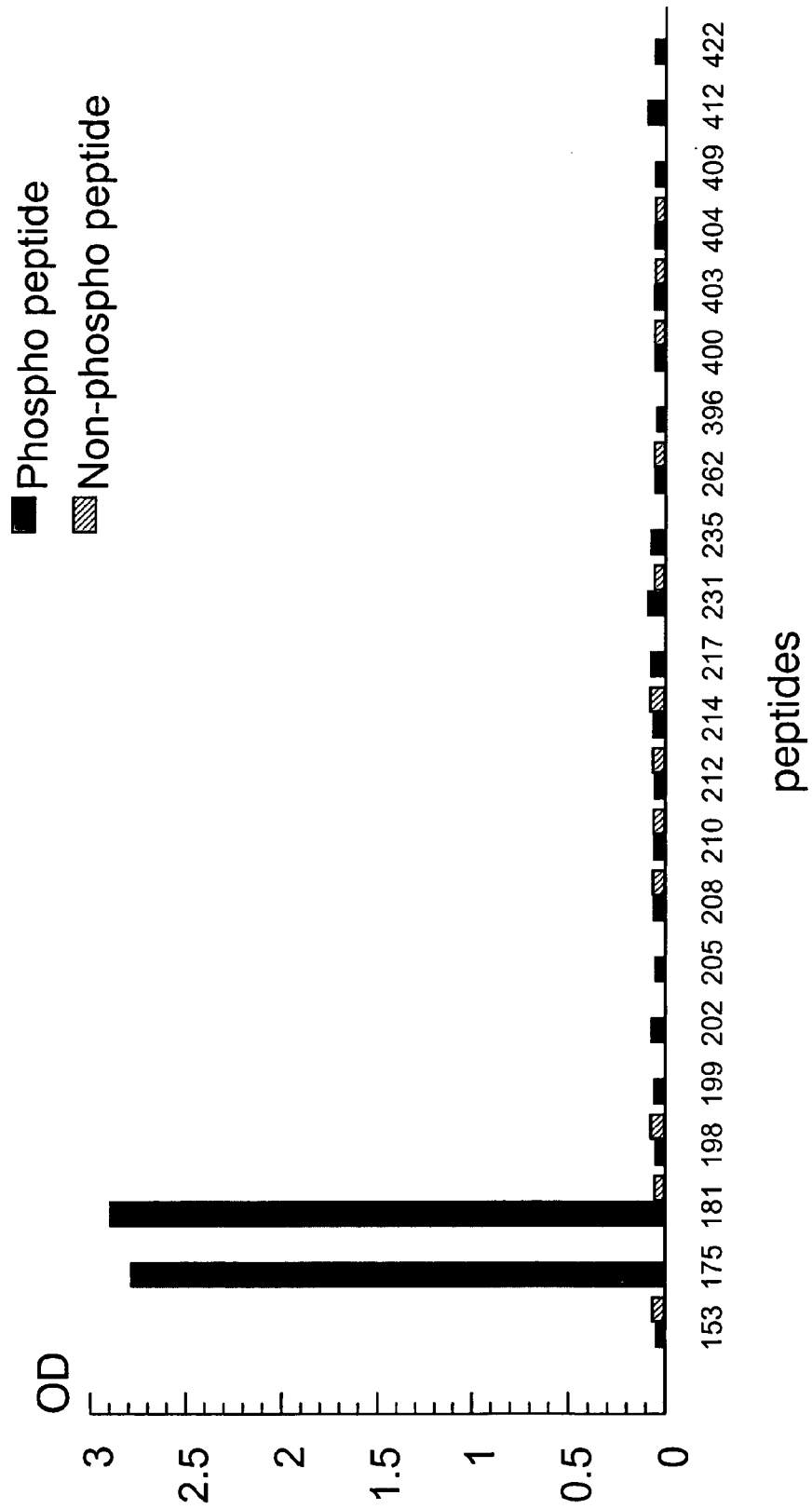
FIG. 2. Specificity of the AT270 antibody for phospho-Thr 181 as defined by screening synthetic phosphopeptides. Biotinylated phosphopeptides were captured on streptavidin-coated plates at a concentration of 1 µg/ml. AT270 was detected via a peroxidase-coupled secondary antibody. The sequences of the peptides are shown in Table 1.

The specificity of the phospho-dependent antibody, AT270, was confirmed on synthetic phospho-peptides covering 22 phosphorylation sites on tau. The sequences of these peptides are summarized in Table 1. Non-phosphorylated peptides corresponding to 12 of these sites were analyzed in parallel (FIG. 2). AT270 only reacted with phospho-peptides containing phospho-Thr 181 and/or phospho-Thr 175. When these peptides were titrated out in a capturing assay, AT270 was 18-fold less reactive on a molar basis with the peptide containing phospho-Thr 175 compared with that of phospho-Thr 181 (results not shown). Finally the minimal epitope was defined using biotinylated phosphorylated peptides 15 amino acids-long covering the region 166-196. Immunoreactive peptides are shown in FIG. 1c, and the minimal epitope of AT270 was ProProAlaProLysThr(p)Pro (position 176-182) (SEQ ID NO 2).

1.5 Design of Phospho-peptide and Determination of the Degree of Phosphorylation Using this peptide information, a phospho-peptide was synthesized covering the position 154 to 187. This sequence covers the epitope of HT7 (159-163) and AT270 (176-182) and an additional 5 amino acids N-terminal to the HT7 epitope and C-terminal of the AT270 epitope. The exact concentration of the phospho-peptide was determined using amino acid analysis (Blennow et al., 1995). Based upon this concentration, the dynamic range of a peroxidase-based ELISA is between 5 and 300 pM using precision profiling. The intra-assay and interassay coefficients of variation were below 10%.

To determine how the degree of phosphorylation relates to absolute levels of phospho-tau (181) and total tau, five different PHF-tau preparations were simultaneously quantified in the respective assays. PHF-tau was prepared according to Goedert et al. (1992) using 1% N-lauroylsarcosinate to selectively precipitate PHF-tau from a brain extracts supernatants. Tissue from temporal cortex (PHF-A-D) or hippocampus (PHF-E) of AD patients was obtained from the Born-Bunge Brain bank (Dr P. Cras, Antwerp, Belgium).

Figure 3:
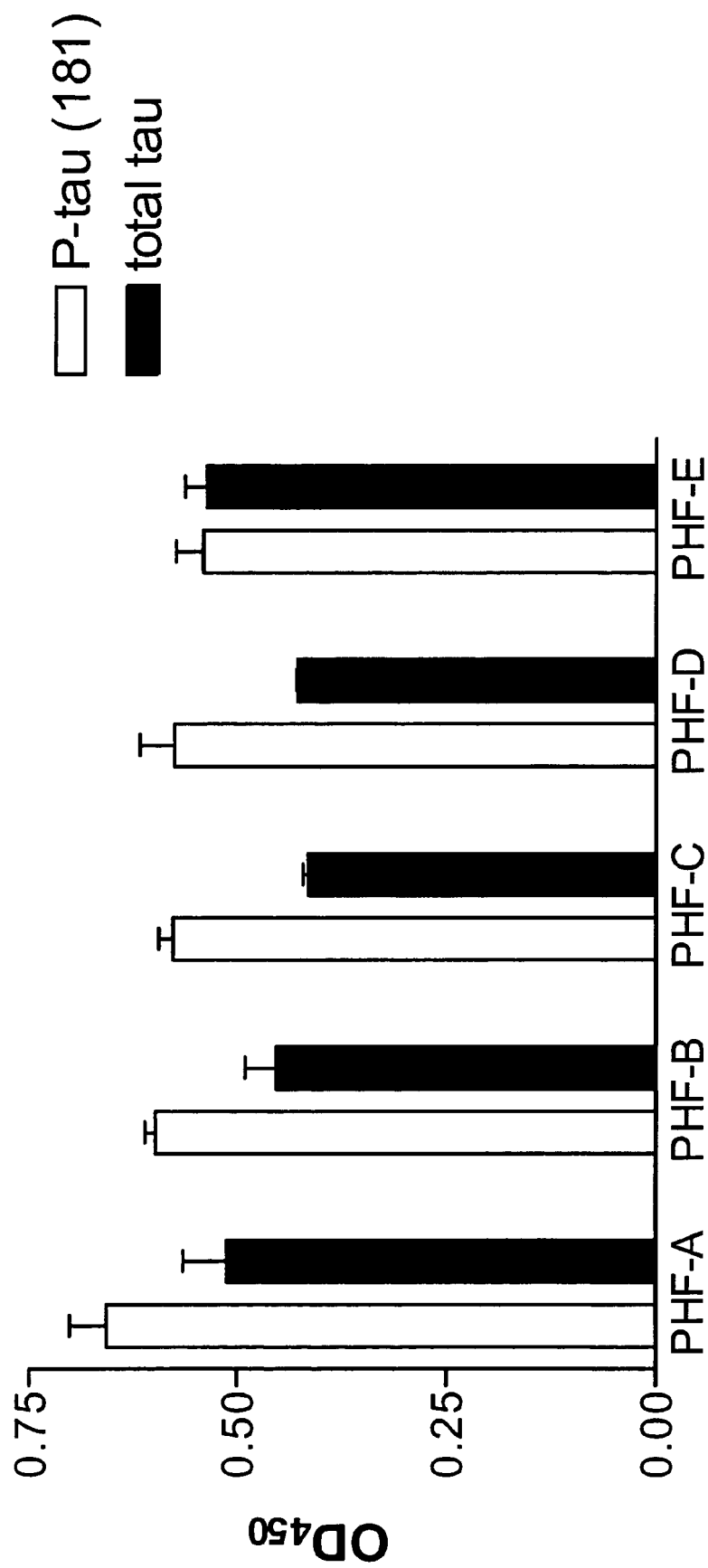
FIG. 3. Relationship of phospho-tau levels, determined by the HT7-AT270 assay, and total tau levels (AT120-(HT7-BT2) assay). Several PHF-tau preparations were assayed at different dilutions. The figure shows the raw data as assayed in duplicate on two different plates from the dilution of the PHF-tau preparation which corresponds to approximately 0.5 $OD_{450}$. Bars on the graph are standard deviations. PHF-A through D are derived from frontotemporal cortex, while PHF-E is prepared from a hippocampal region of an Alzheimer brain.

As shown in FIG. 3, the degree of phosphorylation of phospho-Thr 181 was different between the PHF-tau preparations. Assuming that the PHF-tau preparation with the highest phospho-tau levels has a degree of phosphorylation close to 100%, the ratio phospho-tau (181)/total tau overestimates the degree of phosphorylation at least 3.3-fold. Nevertheless, taking into account that the ratio of phospho-tau (181)/total tau overestimates the degree of phosphorylation, the phosphorylation status of Thr 181 in tau from CSF-tau is 59%±18% (1.952/3.3) at most, which is in close agreement with the phosphorylation status of Thr 181 on brain-derived tau under normal conditions (20-30%; Watanabe et al., 1993; Matsuo et al., 1994).

Example 2

Use of the Phospho-peptide for Standardization in an Assay to Determine Phospho-Tau (181) in Patients with Alzheimer's Disease, Frontotemporal Dementia and/or Vascular Dementia

2.1 Patients

Included in the study were 18 patients with FTD (age range 48-77 years), 60 patients with AD (age range possible 68-88 years; probable 58-90 years), 17 patients with subcortical artheriosclerotic encephalopathy (SAE; a putative form of vascular dementia) (age range 67-84 years), 15 patients with PD (age range 59-82 years), and 17 controls (age range 68-80 years). Their characteristics are summarized in table 2.

All patients included in the study had a clinical diagnosis of FTD, AD, SAE, PD and were consecutively recruited from prospective longitudinal studies on patients with dementia or PD. Clinical diagnoses were established and CSF sampling was performed. Then neurochemical analyses were performed at the Institute of Clinical Neuroscience, Sahlgrenska University Hospital, Mölndal, Sweden. Patients with unspecified dementia (e.g. mixed dementia), a history of severe psychiatric disease (e.g. schizophrenia), chronic alcoholism, distinct non-degenerative neurological disease (e.g. normotensive hydrocephalus), a history of severe head injury, severe infections in the CNS, systemic disease (e.g. malignant tumors) and secondary causes (e.g. hypothyreosis) for dementia according to the Diagnostic and statistical manual of mental disorders (Association AP, 1987) or biochemical criteria were excluded. Excluded were also patients with large cerebral infarcts and/or multiple lacunas. All included patients underwent a thorough clinical investigation, including medical history, physical, neurological and psychiatric examinations, screening laboratory tests of blood (relevant laboratory tests to exclude other causes of ementia e.g. hypothyroidism), routine analysis of the CSF (e.g. cytology), ECG, chest X-ray, EEG, computerized tomography (CT) or magnetic resonance imaging (MRI) of the brain, investigation of the regional cerebral blood flow (CBF), using either single photon emission computerized tomography (SPECT) or [133]Xenon inhalation technique (Cortexplorer; Risberg and Gustafson, 1983).

FTD was diagnosed according to the Lund/Manchester criteria (Brun et al., 1994) as previously described (Sjögren et al., 1997). None of the FTD patients had signs of infarcts, and only mild white-matter changes were found in some FTD patients.

The diagnosis of 'probable AD' was made by exclusion, in accordance with the NINCDS-ADRDA criteria (Mc Khann et al., 1984). The AD patients were divided into one group with probable AD and one with possible AD, as defined by the NINCDS-ADRDA criteria.

The diagnostic criteria for SAE were all of the following: a) mental deterioration (predominantly asteno-emotional disorder and frontal cognitive dysfunction; b) gait disturbance (ataxia and/or motor dysfunction); c) focal neurological signs; d) vascular risk factors such as hypertension and diabetes, or presence of systemic vascular disease; e) at MRI or CT, bilateral multiple of diffuse subcortical—paraventricular deep white matter changes (>2 mm), lacunar infarctions, an enlarged ventricular system and absence of more than one cortical infarction. The criteria were compatible with those suggested by others (Bennett et al., 1990). Fifteen of the SAE patients had no cortical infarction; the remaining four had one cortical infarction.

The diagnosis of PD was made according to recommendations by Langstron and Koller (1991a, b). All the PD patients showed at least two of the three features bradykinesia, rigidity and resting tremor, and all the PD patients were responsive to L-dopa treatment. No patients with PD showed any signs of dementia, and they all had a Mini-Mental State Examination (MMSE) (Folstein et al., 1975) score of 27 or above.

All the clinical diagnoses were made by physicians without knowledge of the results of the biochemical analyses and vice versa. None of the patients were currently treated for dementia (e.g. with cholinesterase inhibitors).

In the demented patients, the degree of dementia was evaluated using the MMSE (Folstein et al., 1997).

The normal controls and the patients with PD were included in the analysis of the sensitivity and specificity of the potential marker.

The control group consisted of individuals without history, symptoms or signs of psychiatric or neurological disease, malignant disease or systemic disorders (e.g. rheumatoid arthritis, infectious disease). MMSE was used to evaluate their cognitive status, and those with scores below 28 were excluded.

The Ethics Committees of the Universities of Göteborg, Lund/Malmö and Linköping, Sweden, approved the study. All the patients (or their nearest relations) and controls gave their informed consent to participating in the study, which was conducted in accordance with the provisions of the Helsinki Declaration.

2.2 CSF Analyses

On all patients and controls, lumbar puncture was performed at the L3/L4 or L4/L5 interspace. The first 12 mL of CSF was collected in polypropylene tubes and gently mixed to avoid gradient effects (Blennow et al., 1993). At the same time, a serum sample was taken. All CSF samples with more than 500 erythrocytes per µl were excluded. The CSF and serum samples were centrifuged at 2000×g for 10 min. to eliminate cells and other insoluble material. Aliquots were then stored at −80° C. until biochemical analysis.

Quantitative determination of serum and CSF albumin was performed by nephelometry, using the Behring Nephelometer Analyzer (Behringwerke AG, Marburg, Germany). The CSF/serum albumin ratio (Tibbling et al., 1977) was calculated as [CSF-albumin (mg/L)/serum-albumin (g/L)] and was used as the measure of blood-brain barrier (BBB) function.

CSF-tau was determined using a sandwich ELISA (INNOTEST hTau-Ag, Innogenetics, Gent, Belgium), constructed to measure total tau (both normal tau and PHF-tau), as described previously in detail (Vandermeeren et al., 1993b; Blennow et al., 1995).

The level of phospho-tau (181) was determined by the INNOTEST phospho-tau (181P) as described above.

2.3 Statistical Analysis

All variables were normally distributed and therefore parametric statistics were used for group comparisons regarding the effect variables (CSF-tau and CSF-phospho-tau). A fully factorial multiple ANOVA was performed with CSF-tau and CSF-phospho-tau respectively as dependent variables, age, duration and severity of dementia as covariates, and diagnostic category (probable and possible AD, FTD, PD, SAE, and normal aging) as factor. Factors that did not contribute to the variance were excluded from the analysis and recalculation was performed. Post-hoc comparisons were performed using Turkey's post-hoc test for unequal n's.

The mean age was significantly lower in PD ($p<0.001$) and probable AD ($p<0.05$) compared to possible AD. Patients with probable AD were significantly more demented than patients with possible AD ($p<0.05$). No differences were found between any of the patient or control groups regarding the CSF/serum albumin ratio (for the dementia groups only), and gender (table 2).

Figure 4:
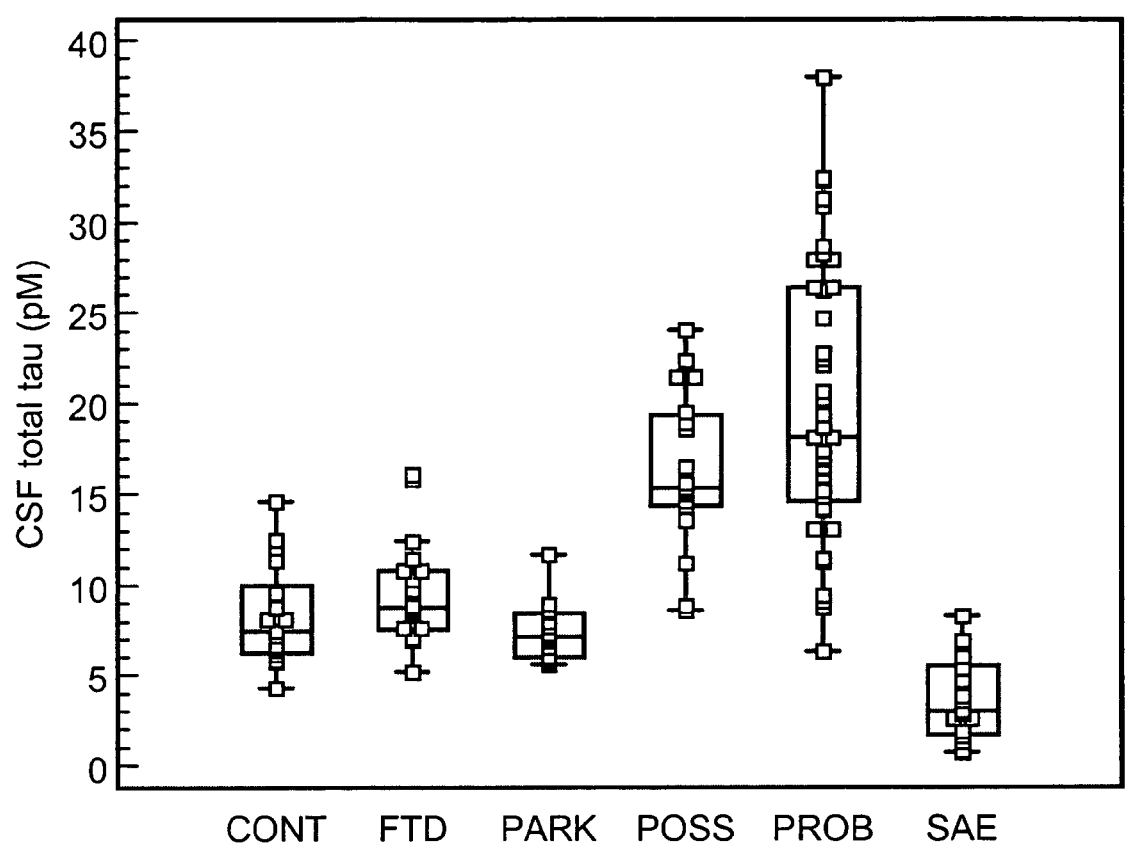
FIG. 4. Scatterplot of CSF-total tau in frontotemporal dementia, Parkinson's disease, Alzheimer's disease and subcortical artheriosclerotic encephalopathy.

2.4 CSF-total Tau and CSF-Phospho-tau (181) in Dementia, Parkinson's Disease and Normal Aging CSF-tau was significantly increased in probable AD and possible AD compared to FTD ($p<0.001$), PD ($p<0.001$), SAE ($p<0.001$), and controls ($p<0.001$), and in FTD compared to SAE ($p<0.01$) (table 3; FIG. 4).

Figure 5:
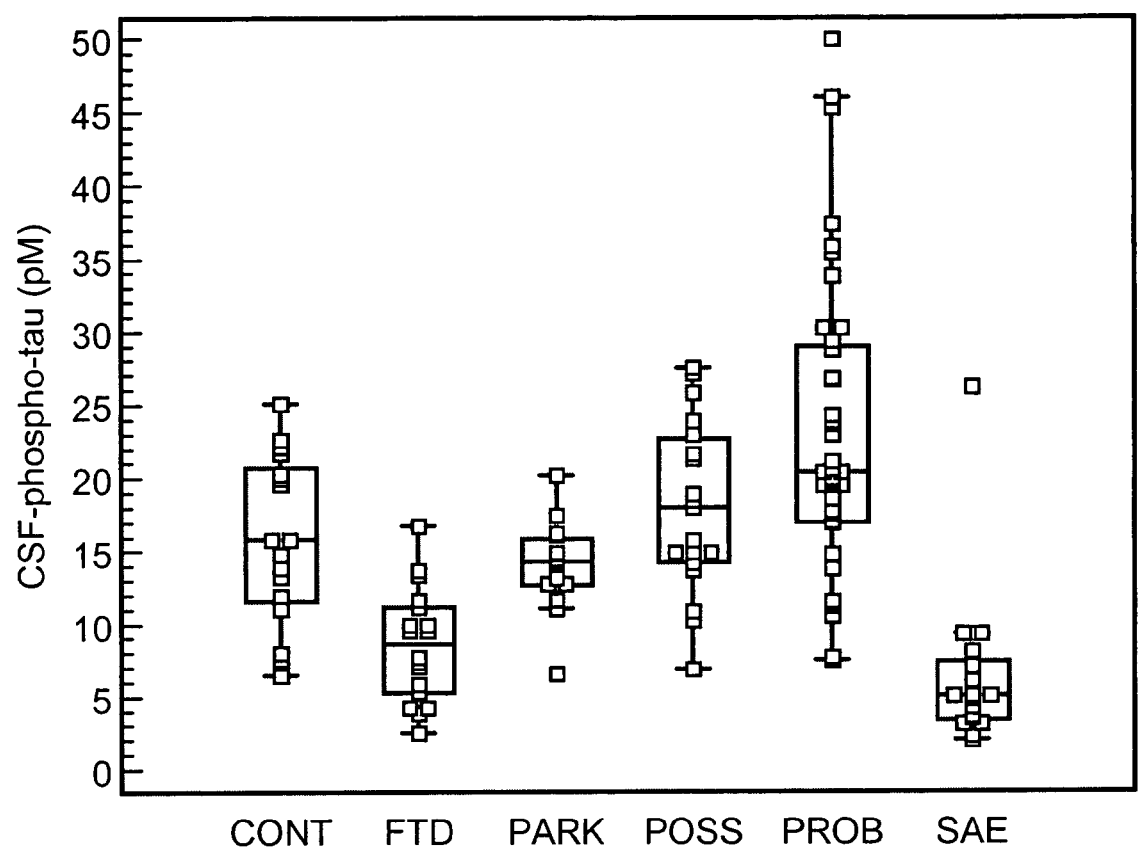
FIG. 5. Scatterplot of CSF-phospho-tau (181) in frontotemporal dementia, Parkinson's disease, Alzheimer's disease and subcortical artheriosclerotic encephalopathy.

CSF-phospho-tau (181) was significantly increased in probable AD compared to FTD ($p<0.001$), PD ($p<0.001$), SAE ($p<0.001$), and controls ($p<0.0079$), and in possible AD compared to FTD ($p<0.001$), and SAE ($p<0.001$), but not compared to controls. Furthermore, the CSF-phospho-tau (181) was also significantly decreased in FTD ($p<0.0001$) and in SAE ($p<0.0001$) as compared to controls (table 3; FIG. 5).

Figure 6:
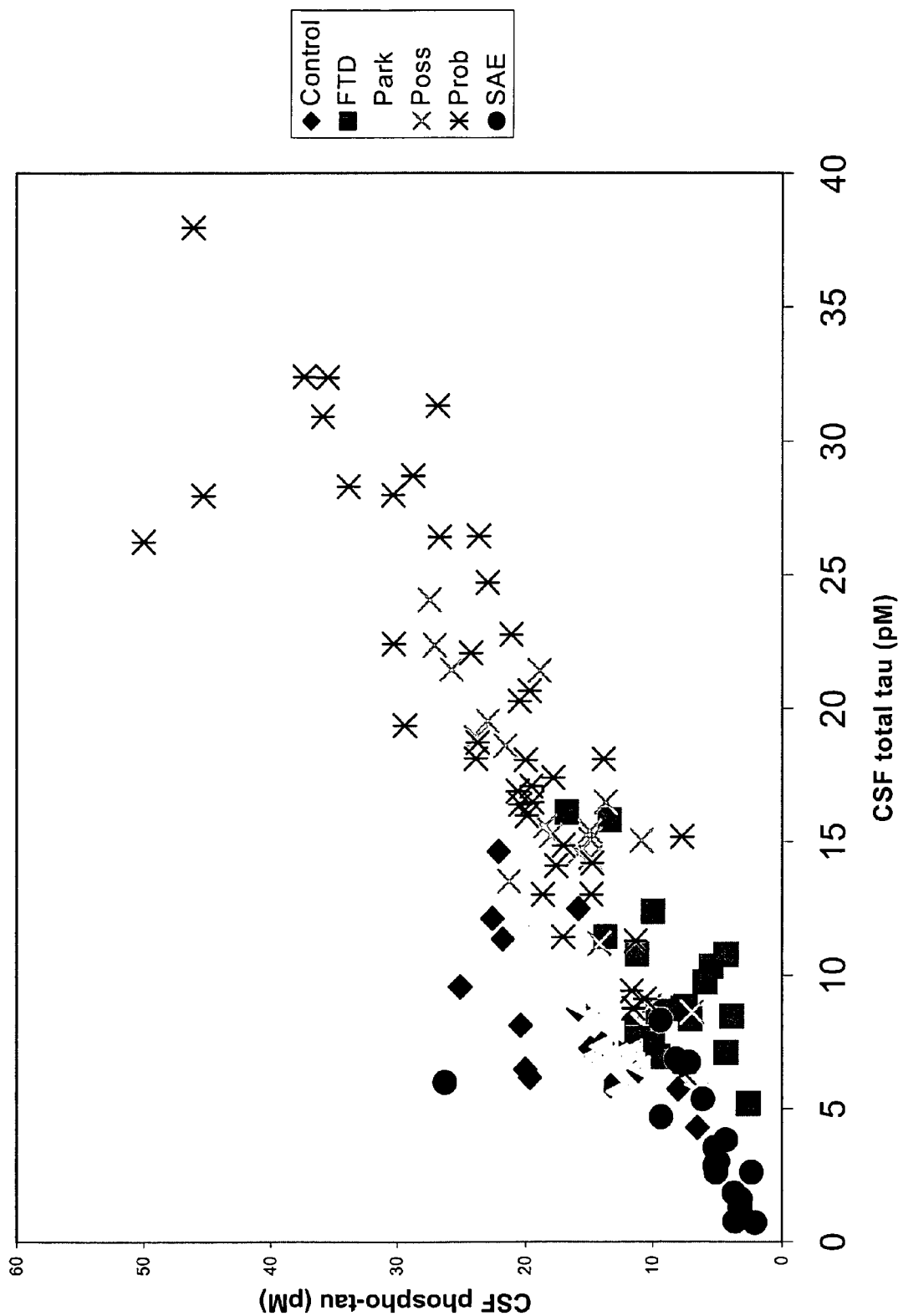
FIG. 6. Plot of correlation between CSF-total tau and CSF-phospho-tau (181), with all individuals in the study included.

CSF-tau and CSF-phospho-tau (181) was positively correlated in all diagnostic groups (probable and possible AD: $r=0.86$, $p<0.001$; FTD: $r=0.66$, $p<0.01$; SAE: $r=0.58$, $p<0.05$; PD: $r=0.62$, $p<0.05$; controls: $r=0.65$, $p<0.01$; FIG. 6).

Figure 7:
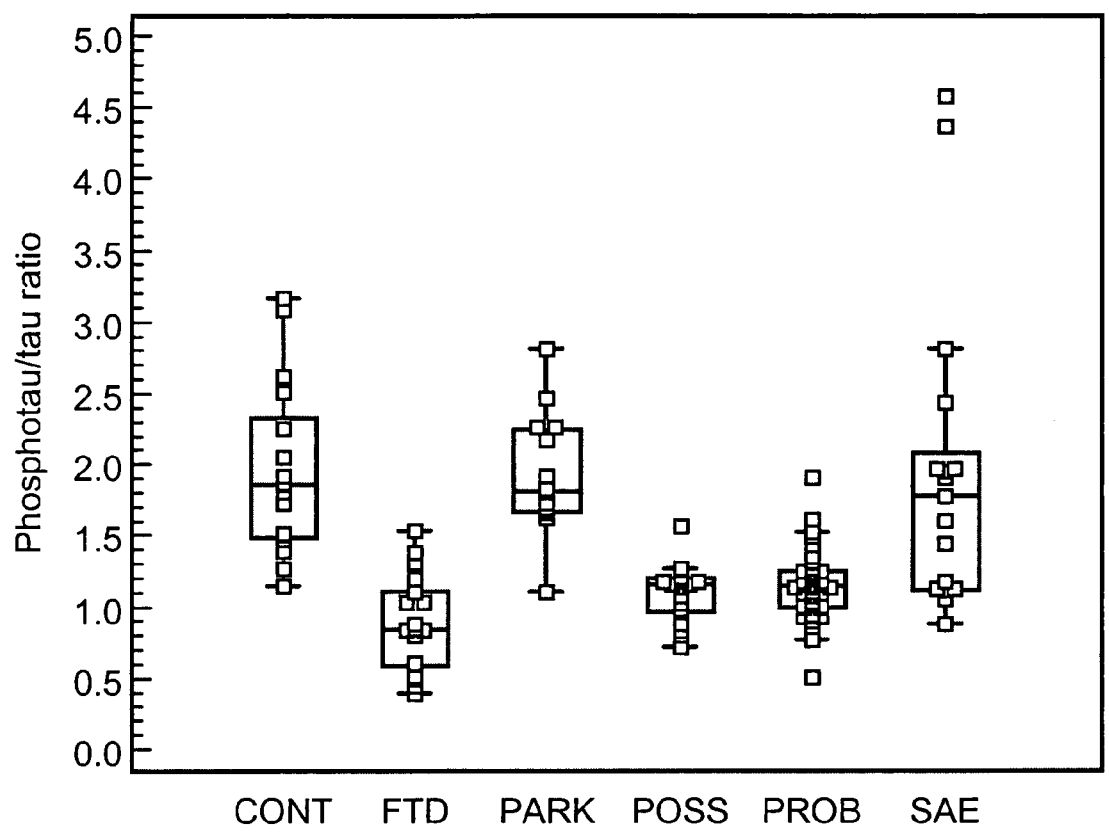
FIG. 7. Scatterplot of phospho-tau (181)/total tau ratio in CSF from patients with frontotemporal dementia, Parkinson's disease, Alzheimer's disease and subcortical artheriosclerotic encephalopathy.

A CSF-phospho-tau (181)/CSF-total tau ratio was calculated and found to be significantly decreased in probable AD ($p<0.001$; 1.16±0.24), possible AD ($p<0.001$; 1.10±0.20), and FTD ($p<0.001$; 0.88±0.34) compared to controls ($p<0.001$ for all three groups; 1.95±0.60), PD ($p<0.001$ for all three groups; 1.92±0.42), and SAE ($p<0.001$ for all three groups; 1.96±1.08) (table 3; FIG. 7).

Example 3

Determination of the CSF-phospho Tau (181) and CSF-total Tau Level in Patients with Alzheimer's Disease Versus Patients with Acute Ischemic Stroke

3.1 Patients

CSF-total tau and CSF-phospho-tau (181) were examined in longitudinal CSF samples from 22 patients, 16 men and 6 women, mean age±SD, 65.7±9.2 years, with an acute ischemic stroke. All patients were evaluated in a standardized way, as described previously (Tarkowski et al., 1999). When possible, CSF samples were collected on five occasions; at income day 0-1 (n=9), day 2-3 (n=18), day 7-9 (n=22), three weeks (n=21) and 3-5 months (n=21).

Also 54 patients with probable AD, 25 men and 29 women, mean age+SD, 73.3+7.4 years, and 17 healthy controls, 4 men and 13 women, mean age+SD, 68.6+7.5 years were studied. The mean age was significantly ($p<0.05$) higher in the AD than in the control group. The diagnosis of "probable AD" was made by exclusion, according to the NINCDS-ADRDA criteria (McKhann et al., 1984). The clinical evaluation and diagnostic procedure have been described in detail elsewhere (Andreasen et al., 1998, 1999). The degree of dementia was evaluated using the MMSE (Folstein, 1975), and was 23.8+4.4 in the AD group. The control group consisted of individuals without history, symptoms or signs of psychiatric or neurological disease, malignant disease or systemic disorders. Individuals with MMSE scores below 28 were not included. All clinical diagnoses were made without knowledge of the results of the biochemical analyses and vice versa.

The stroke patients were examined by computerized tomography (CT) and magnetic resonance imaging (MRI) about 1 month after stroke, as described in detail previously (Tarkowski et al, 1999). The size (in $cm^2$) was determined by CT and the volume (in mL) by MRT.

The Kruskal-Wallis test was used for comparisons between three or more groups, and if significant, the Mann-Whitney U-test for comparisons between two groups. The Spearman correlation coefficient was used for correlations.

The Ethics Committees of the Universities of Göteborg and Umeå approved the study. All patients (or their nearest relatives) and controls gave their informed consent to participate in the study, which was conducted according to the provisions of the Helsinki Declaration.

3.2 CSF Analyses

A lumbar puncture was performed in the L3/L4 or L4/L5 interspace. The first 12 mL of CSF was collected in polypropylene tubes and gently mixed to avoid possible gradient effects (Blennow, 1993). CSF samples with more than 500 erythrocytes per µl were excluded. The CSF samples were centrifuged at 2000×g for 10 min. to eliminate cells and other insoluble material, and aliquots were then stored at −80° C. pending biochemical analyses.

The level of CSF-tau was determined using a sandwich ELISA (Innotest hTAU-Ag, Innogenetics, Gent, Belgium), constructed to measure total tau (both normal tau and PHF-tau), as described in detail previously (Vandermeeren et al., 1993b; Blennow et al., 1995). The level of CSF-phospho-tau (181) was determined by the INNOTEST phospho-tau (181P) as described above.

Figure 8:
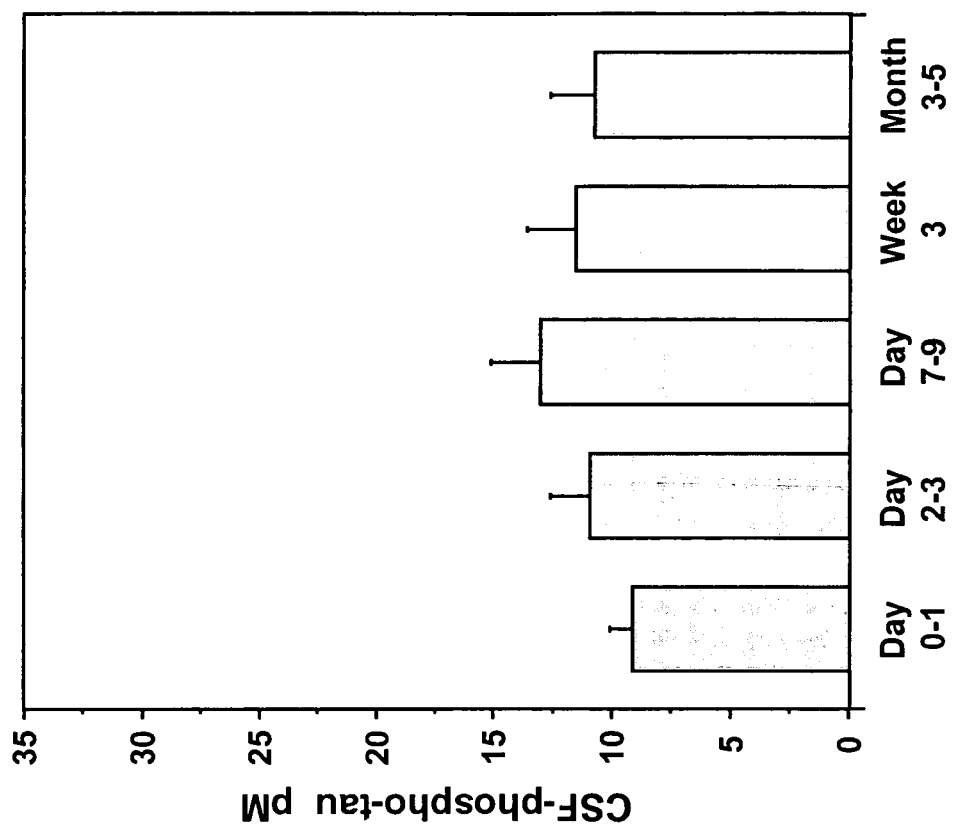
FIG. 8. CSF-total-tau (left) and CSF-phospho-tau (181) (right) at different time points after acute stroke. Staples are means and bars SD. Number of samples at different time points: day 0-1: n=9, day 2-3: n=18, day 7-9: n=22, week 3: n=21, month 3-5: n=21. Significance compared with day 0-1: for CSF-tau: day 2-3: p=0.002, day 7-9: p<0.0001, week 3: p<0.0001, month 3-5: p=0.035; for CSF-phospho-tau: No significant differences at any time point compared with day 0-
Figure 8:
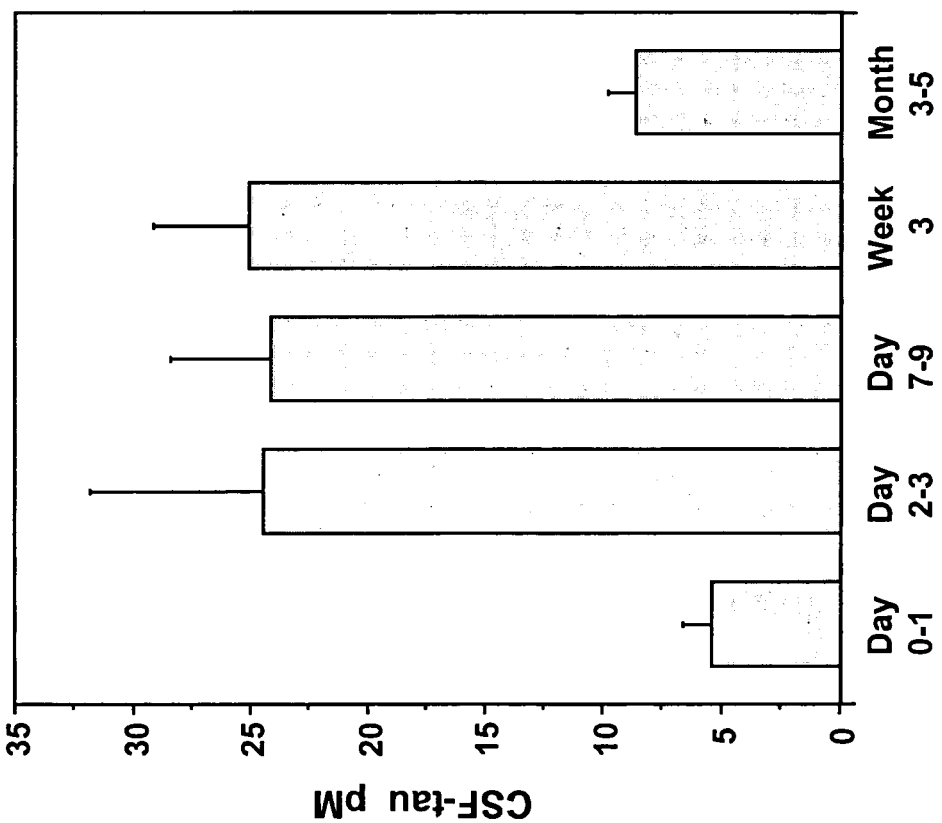
Figure 9:
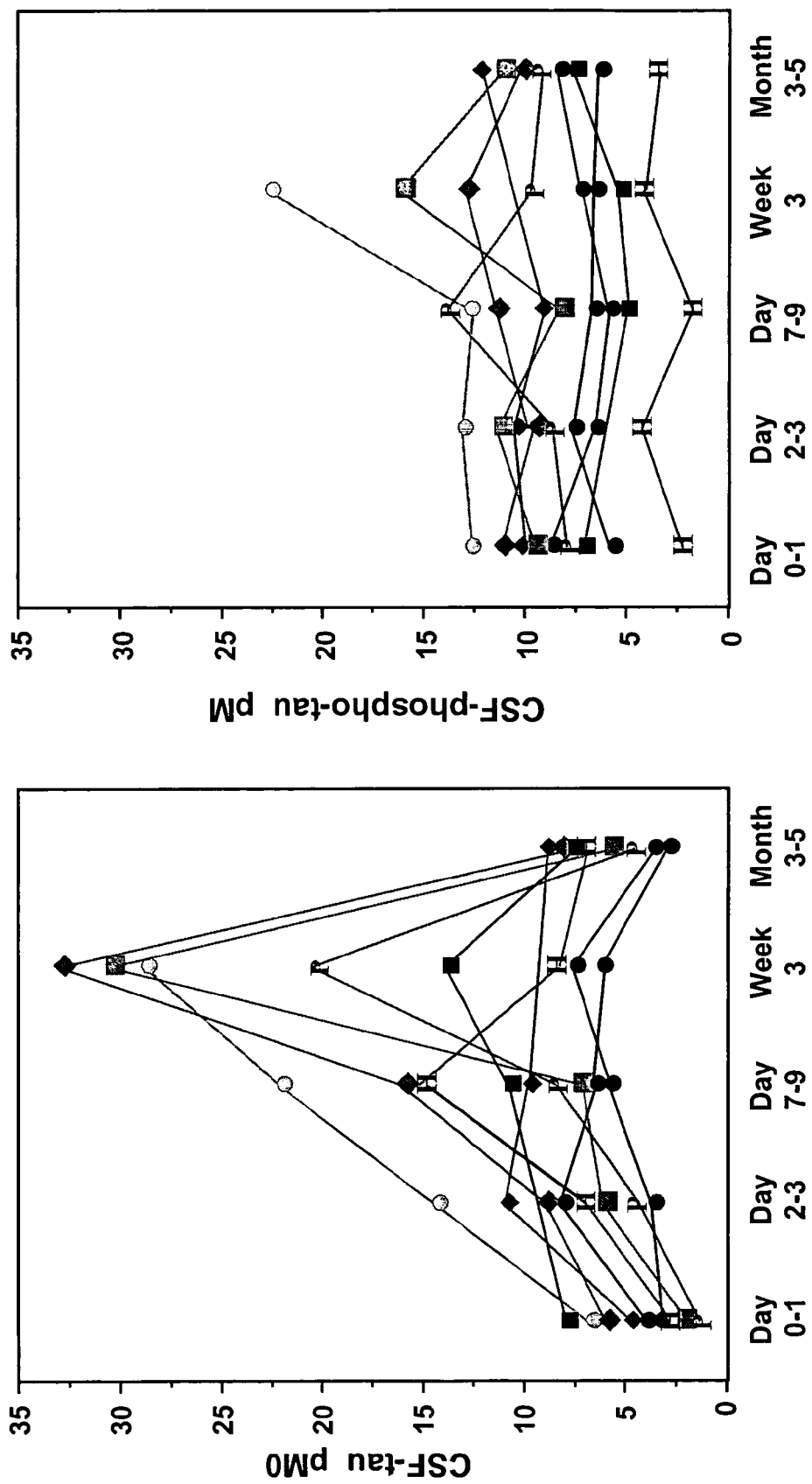
FIG. 9. Individual values for CSF-total-tau (left) and CSF-phospho-tau (181) (right) at different time points for the nine patients of which CSF samples were taken at day one.

3.3 CSF-phospho Tau (181) and CSF-total Tau in Patients with Alzheimer's Disease and in Patients with Stroke In the stroke patients, CSF-total-tau showed a marked increase at day 2-3 (24.4+7.4 pM; $p=0.002$) after the acute stroke as compared with day 0-1 (mean+SEM 5.4+1.2 pM), and stayed elevated at day 7-9 (24.1+4.3 pM; $p<0.0001$) and after three weeks (25.0+4.1 pM; $p<0.0001$) and then returned to normal levels after 3-5 months (8.5+1.2 pM; $p=0.35$) (FIG. 8). The individual values for CSF-total tau for the nine patients with CSF samples taken at baseline are given in FIG. 9.

In contrast, there was no significant change in CSF-phospho-tau (181) between baseline (mean+SEM 9.1+3.1 pM) and day 2-3 (10.9+1.0 pM), day 7-9 (13.0+2.1 pM), three weeks (11.5+2.0 pM) or 3-5 months (10.6+2.0 pM) (FIG. 8). The individual values for CSF-phospho-tau (181) for the nine patients with CSF samples taken at baseline are given in FIG. 9.

CSF-total tau was significantly increased in probable AD (mean+SD 14.4+5.5 pM) compared to controls (8.3+2.8 pM) ($p<0.0001$). Also CSF-phospho-tau (181) was significantly increased in probable AD (20.5+6.5 pM) compared to controls (15.9+5.7 pM) ($p<0.05$).

Figure 10:
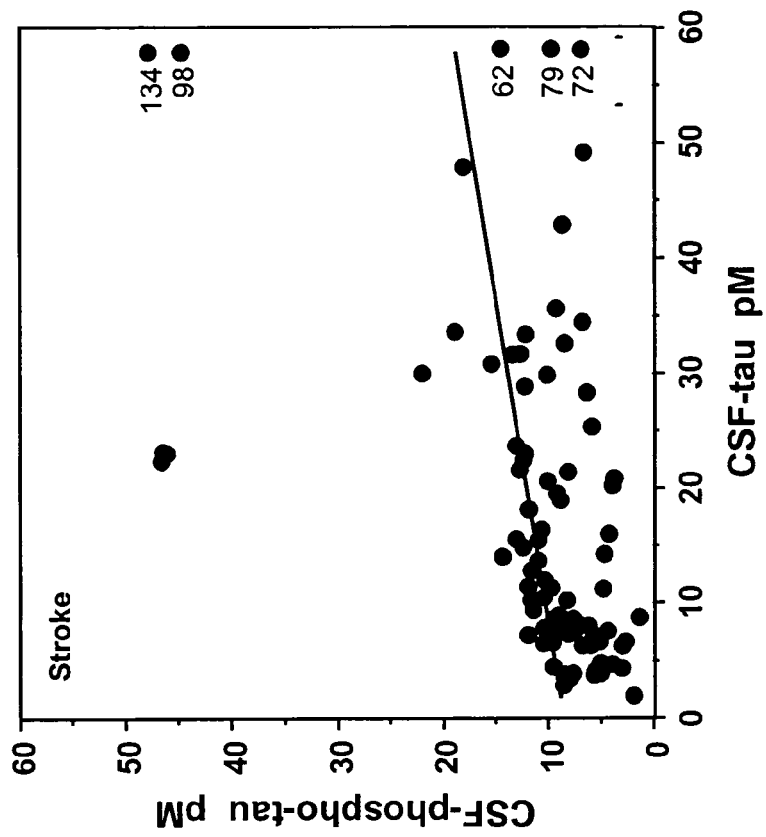
FIG. 10. Correlation between CSF-total-tau and CSF-phospho tau (181) in patients with Alzheimer's disease (n=54) and controls (n=17) (left), and in patients with acute stroke (n=22, number of samples=91) (right).
Figure 10:
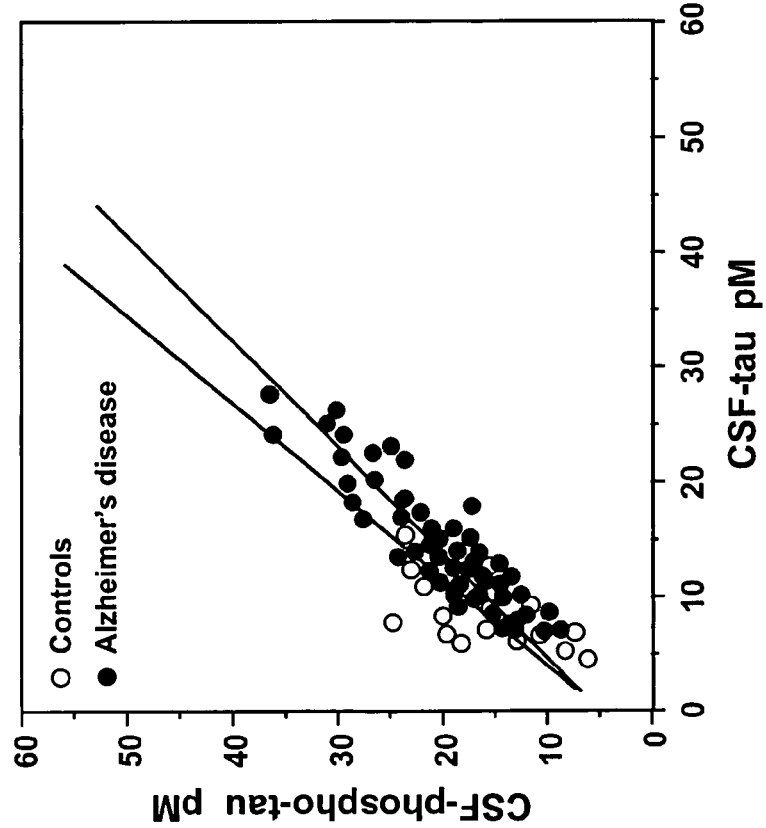

CSF-total tau and CSF-phospho-tau (181) were positively correlated in the AD ($r=0.93$; $p<0.0001$) and in the control ($r=0.72$, $p<0.01$) groups (FIG. 10). In the stroke group, the correlation was higher at day 0-1 ($r=0.63$, $p<0.001$) and after 3 months ($r=0.80$), than at day 2-3 ($r=0.54$), day 7-9 ($r=0.58$) and especially after three weeks ($r=0.15$).

From FIG. 10 it is clear that there is a difference between the ratio CSF-phospho tau (181)/CSF-total tau for Alzheimer's disease patients compared to stroke patients. Regression analysis for values obtained from Alzheimer's disease patients ($y=0.82x+4.39$, $r=0.90$, $p<0.0001$) and from Stroke patients ($y=0.17x+8.09$, $r=0.415$, $p<0.0001$) revealed a significant difference ($p<0.001$).

There was a positive correlation between the size of the infarct as measured by CT and the maximum level of CSF-total tau ($r=0.72$; $p<0.01$), while the correlation to CSF-phospho-tau (181) was not significant ($r=0.349$). There was also a positive correlation between the volume of the infarct as measured by MRI and the maximum value of CSF-total tau ($r=0.66$; $p<0.05$), while the correlation to CSF-phospho-tau (181) was not significant ($r=0.59$).

REFERENCES

Andreadis A., Brown W. and Kosik K. (1992) Structure and novel exons of the human tau gene. Biochem. 31: 10626-10633.

Andreasen N., Vanmechelen E., Van de Voorde A., Davidsson P., Hesse C., Tarvonen S., Räihä I., Sourander L., Winblad B., Blennow K. (1998) Cerebrospinal fluid tau protein as a biochemical marker for Alzheimer's disease: a community-based follow-up study. J Neurol. Neurosurg. Psychiatry 64: 298-305.

Andreasen N., Minthon L., Clarberg A., Davidsson P., Gottfries J., Vanmechelen E., Vanderstichele H., Winblad B., Blennow K. (1999) Sensitivity, specificity and stability of CSF-tau in AD in a community-based patient sample. Neurology 53: 1488-1494.

Arbit E., Cheung N. K., Yeh S. D., Daghighian F., Shang J. J., Cordon-Cardo C., Pentlow K., Canete A., Finn R. and Larson S. M. (1995) Quantitative studies of monoclonal antibody targeting to disialogangliosid GD2 in human brain tumors. Eur. J. Nucl. Med. 22: 419-426.

Association AP (1987) Diagnostic and Statistical Manual of Mental Disorders, 3$^{rd}$ ed. (revised). Cambridge University Press, Washington DC., US.

Atherton and Shepard (1989) Solid phase peptide synthesis. IRL Press, Oxford, UK.

Bennett D. A., Wilson R. S., Gilley D. W. and Fox J. H. (1990) Clinical diagnosis of Binswanger's disease. J. Neurol. Neurosurg. Psychiatry 53: 961-965.

Binder L. I., Frankfurther A. and Rebhun L. I. (1985) The distribution of tau in the mammalian central nervous system. J. Cell Biol. 101: 1371-1378.

Blennow K., Fredman P., Wallin A., Gottfries C.-G., Langstrom L. and Svennerholm L. (1993) Protein analysis in cerebrospinal fluid. I. Influence of concentration gradients for proteins on cerebrospinal fluid/serum albumin ratio. European Neurology 33: 126-128.

Blennow K., Wallin A., Agren H., Spenger C., Siegfried J. and Vanmechelen E. (1995) Tau protein in cerebrospinal fluid: a biochemical marker for axonal degeneration in Alzheimer disease? Mol. Chem. Neuropathol. 26: 231-245.

Bramblett G., Trojanowski J. and Lee V. (1992) Regions with abundant neurofibrillary pathology in human brain exhibit a selective reduction in levels of binding-competent tau and accumulation of abnormal tau isoforms (A68 proteins). Lab. Invest. 66: 212-222.

Bramblett G., Goedert M., Jakes R., Merrick S., Trojanowski J. and Lee V. (1993) The abnormal phosphorylation of tau at Ser396 in Alzheimer's disease recapitulates phosphorylation during development and contributes to reduced microtubule binding. Neuron. 10: 1089-1099.

Brion J., Passareiro J., Nunez J. and Flament-Durand J. (1985) Mise en evidence immunologique de la proteine tau au niveau des lesions de degenerescence neurofibrillaire de la maladie d'Alzheimer. Arch. Biol. 95: 229-235.

Brun A. (1987) Frontal lobe degeneration of non-Alzheimer type. I. Neuropathology. Arch. Gerontol. Geriatr. 6: 193-208.

Brun A. (1993) Frontal lobe degeneration of non-Alzheimer type revisited. Dementia 4: 126-131.

Brun A., Englund B., Gustafsson L., Passant U., Mann D. M. A., Neary D. and Snowden J. S. (1994) Clinical and neuropathological criteria for frontotemporal dementia. J. Neurol., Neurosurgery and Psych. 57: 416-418.

Buee L., Delacourte A. (1999) Comparative biochemistry of tau in progressive supranuclear palsy, corticobasal degeneration, FTDP-17 and Pick's disease. Brain Pathol. 9: 681-693.

Delacourte A. and Défossez A. (1986) Alzheimer's disease: Tau proteins, the promoting factors of microtubule assembly, are major components of paired helical filaments. J. Neurol. Sci. 76: 173-180.

Delacourte A., Flament S., Dibe E., Hublau P., Sablonniere B., Hemon B., Sherrer V. and Defossez A. (1990) Pathological proteins Tau64 and 69 are specifically expressed in the somatodendritic domain of the degenerating cortical neurons during Alzheimer's disease. Acta Neuropathol. 80: 111-117.

Delacourte A., Buée L. and Vermersch P. (1996) Immunochemistry in frontotemporal dementia. In: Pasquier F, Lebert F., Scheltens P. (eds.) Frontotemporal dementia. ICG Publications, Dordrecht, The Netherlands. pp. 115-124.

DeLeys R., Hendrickx G., Dekeyser P., Demol H., Raymakers J., Brasseur R., Borremans F., Vanmechelen E. and Van de Voorde A. (1996) Mapping and sequence requirements of the phosphorylation-sensitive epitopes recognized by the monoclonal antibodies Tau1, BT2, and AT8. In: Schneider C. H. (ed.) Peptides in Immunology. John Wiley & Sons, New York, N.Y., US. pp. 239-244.

Ebly E. M., Parhad I. M., Hogan D. B. and Fung T. S. (1994) Prevalence and types of dementia in the very old: results from the Canadian Study of Health and Aging. Neurology 44: 1593-1600.

Flament S. and Delacourte A. (1990) Tau Marker? Nature 346: 6279.

Folstein M., Folstein S. and Mc Hugh P. (1975) "Mini-mental State" A practical method for grading the cognitive state of patients for the clinician. J. Psychol. Res. 12: 189-198.

Ghanbari H., Kozuk T., Miller B. and Riesing S. (1990) A sandwich enzyme immunoassay for detecting and measuring Alzheimer's disease-associated proteins in human brain tissue. J. Clin. Laboratory Anal. 4: 189-192.

Goedert M., Spillantini M. G., Jakes R., Rutherford D. and Crowther R. A. (1989) Multiple isoforms of human microtubule-associated protein tau: sequences and localization in neurofibrillary tangles of Alzheimer's disease. Neuron 3: 519-526.

Goedert M., Spillantini M. G., Cairns N. J. and Crowther R. A. (1992) Tau proteins of Alzheimer paired helical filaments: abnormal phosphorylation of all six brain isoforms. Neuron 8: 159-168.

Goedert M., Jakes R., Crowther R., Six J., Lübke U., Vandermeeren M., Cras P., Trojanowski J. Q. and Lee V. (1993) The abnormal phosphorylation of tau protein at serine 202 in Alzheimer's disease recapitulates phosphorylation during development. Proc. Natl. Acad. Sci. (USA) 90: 5066-5070.

Goedert M., Jakes R., Crowther R. A., Cohen P., Vanmechelen E., Vandermeeren M. and Cras P. (1994) Epitope mapping of monoclonal antibodies to the paired helical filaments of Alzheimer's disease: identification of phosphorylation sites in tau protein. Biochem. J. 301: 871-877.

Goedert M., Crowther R. A., Spillantini M. G. (1998) Tau mutations cause frontotemporal dementias. Neuron 21: 955-958.

Greenberg S. and Davies P. (1990) A preparation of Alzheimer paired helical filaments that displays distinct tau proteins by polyacrylamide gel electrophoresis. Proc. Natl. Acad. Sci. USA 87: 5827-5831.

Grundke-Iqbal I., Iqbal K., Tung Y., Quinlan M., Wisniewski H. and Binder L. (1986) Abnormal phosphorylation of the microtubule-associated protein (tau) in Alzheimer's cytoskeletal pathology. Proc. Natl. Acad. Sci. (USA) 83: 4913-4917.

Gustafson L. (1993) Clinical picture of frontal lobe degeneration of non-Alzheimer type. Dementia 4: 143-148.

Hanger D. P., Betts J. C., Loviny T. L., Blackstock W. P., Anderton B. H. (1998) New phosphorylation sites identified in hyperphosphorylated tau (paired helical filament-tau) from Alzheimer's disease brain using nanoelectrospray mass spectrometry. J. Neurochem. 71: 2465-2476.

Hasegawa M., Morishima-Kawashima M., Takio K., Suzuki M., Titani K. and Ihara Y. (1992) Protein sequence and mass spectrometric analyses of tau in Alzheimer's disease brain. J. Biol. Chem 267: 17047-17054.

Himmler A. (1989) Structure of the bovine tau gene: alternatively spliced transcripts. Mol. Cell Biol. 9(4): 1389-96.

Houbenweyl (1974) Method of organic chemistry. Vol. 15-1 et II. Eds. E Wunch, Thieme, Stuttgart, Germany.

Huang Q., He G., Lan Q., Li X., Qian Z. Chen J. Lu Z. and Du Z. (1996) Target imaging diagnosis of human brain glioma. Clinical analysis of 40 cases. Nucl. Med. Commun. 17: 311-316.

Iqbal K., Grundke-Iqbal I., Smith A., George L., Tung Y. and Zaidi T. (1989) Identification and localisation of a Tau peptide to paired helical filaments of Alzheimer's disease. Proc. Natl. Acad. Sci. (USA) 86: 5646-5650.

Kondo J., Honda T., Mori H., Hamada Y., Miura R., Ogawara M. and Ihara Y. (1988) The carboxyl third of tau is tightly bound to paired helical filaments. Neuron 1: 827-834.

Kosik K. S., Joachim C. L. and Selkoe D. J. (1986) Microtubule-associated protein tau is a major antigenic component of paired helical filaments in Alzheimer's disease. Proc. Natl. Acad. Sci. (USA) 83: 4044-4048.

Ksiezak-Reding H., Liu W. K. and Yen S. H. (1992) Phosphate analysis and dephosphorylation of modified tau associated with paired helical filaments. Brain Res. 597: 209-219.

Langstron J. W. and Koller W. C. (1991a) Preclinical detection of Parkinson's disease. The next frontier: presymptomatic detection. Introduction. Geriatrics 46 Suppl. 1: 5-7.

Langstron J. W. and Koller W. C. (1991b) The next frontier in Parkinson's disease: presymptomatic detection. Neurology 41: 5-7.

Lee V., Balin B., Otvos L. and Trojanowski J. (1991) A68: a major subunit of paired helical filaments and derivatized forms of normal tau. Science 251(4994): 675-8.

Lewis S., Wang D. and Cowan N. (1988) Microtubule-associated protein MAP2 shares a microtubule binding motif with Tau protein. Science 242: 936-939.

Mann D., McDonagh A., Snowden J., Neary D. and Pickering-Brown S. (2000) Molecular classification of the dementias. The Lancet 355: 626.

Matsuo E. S., Shin R. W., Billingsley M. L., Van de Voorde A., O'Connor M., Trojanowski J. Q. and Lee V. M. (1994) Biopsy-derived adult human brain tau is phosphorylated at many of the same sites as Alzheimer's disease paired helical filament tau. Neuron 13: 989-1002.

Mc Khann G., Drachman D., Folstein M., Katzman R., Price D., Stadlan E. M. (1984) Clinical diagnosis of Alzheimer's disease: report on the NINCDS-ADRDA Work group under the auspices of department of health and human services task force on Alzheimer's disease. Neurology 34: 939-944.

Mercken M., Vandermeersen M., Lübke U., Six J., Boons J., Vanmechelen E., Van de Voorde A. and Gheuens J. (1992) Affinity purification of human tau proteins and the construction of a sensitive sandwich enzyme-linked immunosorbent assay for human tau detection. J. Neurochem. 58: 548-553.

Risberg J. and Gustafson L. (1983) $^{133}$Xe cerebral blood flow in dementia and in neuropsychiatry research. In: Magistretti P. L. (ed.) Functional Radionuclide Imaging of the brain. Raven Press, New York, N.Y., US. Pp. 151-159.

Sambrook J., Fritsch E., Maniatis T. (1989) Molecular Cloning: A Laboratory Manual, 2$^{nd}$ Edition, Cold Spring Harbour Laboratory Press, Cold Spring Harbor, N.Y., USA.

Sandrock D., Verheggen R., Helwig A. T., Munz D. L., Markakis E. and Emrich D. (1996) Immunoscintigraphy for the detection of brain abscesses. Nucl. Med. Commun. 17: 311-316.

Selden S. and Pollard T. (1983) Phosphorylation of microtubule-associated proteins regulates their interaction with actin filaments. J. Biol. Chem. 258(11): 7064-71.

Sjögren M., Edman A. and Wallin A. (1997) Symptomatology characteristics distinguish between frontotemporal dementia and vascular dementia with a dominating frontal lobe syndrome. Int. J. Geriatric Psychiatry 12: 656-661.

Spillantini M. G. and Goedert M. (1998) Tau protein pathology in neurodegenerative diseases. Trends Neurosci. 21: 428-433.

Tamada K., Fujinaga S., Watanabe R., Yamashita R., Takeuchi Y. and Osano M. (1995) Specific deposition of passively transferred monoclonal antibodies against herpes simplex virus type 1 in rat brain infected with the virus. Microbiol-Immunol. 39: 861-871.

Tarkowski E., Rosengren L., Blomstrand C., Jensen C., Ekholm S. and Tarkowski A. (1999) Intrathecal expression of proteins regulating apoptosis in acute stroke. Stroke 30: 321-327.

Tibbling G., Link H. and Ohman S. (1977) Principles of albumin and IgG analyses in neurological disorders. I. Establishment of reference values. Scand. J. Clin. Lab. Invest. 37: 385-390.

Tomlinson B. E. and Corsellis J. A. N. (1984) Ageing and the dementias. In: Hume Adams J., Corsellis J. A. N., Duchen L. W. (eds.) Greenfield's neuropathology. Edward Arnold, London, UK. pp. 951-1025.

Vandermeeren M., Lübke U., Six J. and Cras P. (1993a) The phosphatase inhibitor okadaic acid induces a phosphorylated paired helical filament tau epitope in human LA-N-5 neuroblastoma cells. Neurosci. Lett. 153: 57-60.

Vandermeeren M., Mercken M., Vanmechelen E., Six J., Van de Voorde A., Martin J. J. and Cras P. (1993b) Detection of tau proteins in normal and Alzheimer's disease cerebrospinal fluid with a sensitive sandwich enzyme-linked immunosorbent assay. J. Neruochem. 61: 1828-1834.

Vermersch P., Bordet R., Ledoze F., Ruchoux M. M., Chapon F., Thomas P., Destee A., Lechevallier B. and Delacourte A. (1995) C R Demonstration of a specific profile of pathological Tau proteins in frontotemporal dementia cases. Acad. Sci. 318: 439-445.

Wakabayashi T., Yoshida J., Okada H., Sugita K., Itoh K., Tadokoro M. and Ohshima M. (1995) Radioimaging of human glioma by indium-11 labelled G-22 anti-glioma monoclonal antibody. Noshuyo-Byori 12: 105-110.

Watanabe A., Hasegawa M., Suzuki M., Takio K., Morishima-Kawashima M., Titani, K., Arai T., Kosik K. S. and Ihara Y. (1993) In vivo phosphorylation sites in fetal and adult rat tau. J. Biol. Chem. 268: 25712-25717.

Wood J., Mirra S., Pollock N. and Binder L. (1986) Neurofibrillary tangles of Alzheimer's disease share antigenic determinants with the axonal mirotubule-associated protein tau. Proc. Natl. Acad. Sci. (USA) 83: 4040-4043.

The invention claimed is:

1. A diagnostic kit comprising a phospho-peptide wherein the phospho-peptide consists of 15 to 50 amino acids in length, wherein the phospho-peptide is liable to form an immunological complex with monoclonal antibody HT7 and monoclonal antibody AT270, wherein the phospho-peptide comprises:
   (a) the minimal epitope of HT7: ProProGlyGlnLys (SEQ ID NO: 1); and
   (b) the minimal epitope of AT270: ProProAlaProLysThr (p)Pro (SEQ ID NO:2); and wherein the phospho-peptide is in a container.

2. The diagnostic kit of claim 1 wherein the phospho-peptide comprises the sequence:

ProArgGlyAlaAlaProProGlyGlnLysGlyGlnAlaAsnAlaThr
ArgIleProAlaLysThrProProAlaProLysThr(p)ProProSer
SerGlyGlu (SEQ ID NO:3)

or a variant sequence thereof, wherein said variant sequence comprises SEQ ID NO:1 and SEQ ID NO:2.

3. The diagnostic kit of claim 1 wherein the phospho-peptide comprises the sequence of SEQ ID NO:3.

4. The diagnostic kit of claim 1 wherein the phospho-peptide consists of the sequence of SEQ ID NO:3.

5. The diagnostic kit of claim 1 wherein the phospho-peptide consists of 20 to 50 amino acid residues in length.

6. The diagnostic kit of claim 1 wherein the phospho-peptide consists of 30 to 40 amino acid residues in length.

7. A phospho-peptide comprising:
   (a) the minimal epitope of HT7: ProProGlyGnLys (SEQ ID NO:1); and
   (b) the minimal epitope of AT270: ProProAlaProLysThr (p)Pro (SEQ ID NO:2);
   wherein the phospho-peptide consists of 15 to 50 amino acids in length and wherein the phospho-peptide is liable to form an immunological complex with monoclonal antibody HT7 and monoclonal antibody AT270.

8. The phospho-peptide of claim 7 that comprises the sequence

ProArgGlyAlaAlaProProGlyGlnLysGlyGlnAlaAsnAlaThr
ArgIleProAlaLysThrProProAlaProLysThr(p)ProProSer
SerGlyGlu (SEQ ID NO:3)

or a variant sequence thereof, wherein said variant sequence comprises SEQ ID NO:1 and SEQ ID NO:2.

9. The phospho-peptide of claim 7 comprising the sequence of SEQ ID NO:3.

10. The phospho-peptide of claim 7 consisting of the sequence of SEQ ID NO:3.

11. The phospho-peptide of claim 7 that consists of 20 to 50 amino acid residues in length.

12. The phospho-peptide of claim 7 that consists of 30 to 40 amino acid residues in length.

13. A method for measuring the level of phospho-tau (181) in a sample comprising:
   (a) providing a phospho-peptide described in any one of claims 7 through 12 as a standard for determining the level of phospho-tau (181) by:
   (1) detecting said phospho-peptide in one or more control samples immunologically, wherein the amount or concentration of said phospho-peptide in said control samples is known, thereby obtaining control results;
   (2) quantifying the control results;
   (b) detecting phospho-tau (181) in a sample immunologically; thereby obtaining an experimental result, and quantifying the experimental result; and
   (c) correlating the quantified experimental result with the quantified control results and known control amounts or concentrations to calculate the level of phospho-tau (181) in the sample of step (b).

* * * * *

UNITED STATES PATENT AND TRADEMARK OFFICE
CERTIFICATE OF CORRECTION

PATENT NO. : 7,387,879 B2 Page 1 of 1
APPLICATION NO. : 10/682103
DATED : June 17, 2008
INVENTOR(S) : Eugeen Vanmechelen and Hugo Vanderstichele It is certified that error appears in the above-identified patent and that said Letters Patent is hereby corrected as shown below:

Column 43, Line 52 (claim 7): delete "ProProGlyGnLys" and insert
-- ProProGlyGlnLys --.

Signed and Sealed this

Twenty-sixth Day of August, 2008

JON W. DUDAS
*Director of the United States Patent and Trademark Office*